United States Patent
Davies et al.

(10) Patent No.: US 9,611,456 B2
(45) Date of Patent: *Apr. 4, 2017

(54) PROGENITOR CELLS FROM WHARTON'S JELLY OF HUMAN UMBILICAL CORD

(71) Applicant: Tissue Regeneration Therapeutics Inc., Toronto (CA)

(72) Inventors: John E. Davies, Toronto (CA); Dolores Baksh, Mississauga (CA); Rahul Sarugaser, Toronto (CA); Morris Hosseini, Braunschweig (DE); Antony D. S. Lickorish, Toronto (CA)

(73) Assignee: Tissue Regeneration Therapeutics Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/884,339

(22) Filed: Oct. 15, 2015

(65) Prior Publication Data

US 2016/0032241 A1    Feb. 4, 2016

Related U.S. Application Data

(63) Continuation of application No. 13/903,575, filed on May 28, 2013, which is a continuation of application No. 12/482,963, filed on Jun. 11, 2009, now Pat. No. 8,481,311, which is a continuation of application No. 10/961,919, filed on Oct. 8, 2004, now Pat. No. 7,547,546, which is a continuation-in-part of application No. PCT/CA2004/000182, filed on Feb. 10, 2004.

(60) Provisional application No. 60/446,275, filed on Feb. 11, 2003.

(51) Int. Cl.
    C12N 5/073      (2010.01)
    A61K 35/51      (2015.01)
    C12N 5/0775     (2010.01)
    C12N 5/077      (2010.01)

(52) U.S. Cl.
    CPC ............ *C12N 5/0605* (2013.01); *A61K 35/51* (2013.01); *C12N 5/0653* (2013.01); *C12N 5/0654* (2013.01); *C12N 5/0668* (2013.01); *C12N 2509/00* (2013.01); *C12N 2523/00* (2013.01)

(58) Field of Classification Search
    CPC .. C12N 5/0653; C12N 5/0654; C12N 5/0658; C12N 5/0668
    See application file for complete search history.

(56) References Cited

U.S. PATENT DOCUMENTS 5,919,702 A *   7/1999  Purchio ............. A61L 27/3633
                                              424/93.1
7,122,178 B1   10/2006  Simmons et al.
7,736,892 B2 *  6/2010  Weiss ................ C12N 5/0607
                                              435/325
2002/0045260 A1  4/2002  Hung et al.
2003/0161818 A1  8/2003  Weiss et al.
2004/0136967 A1  7/2004  Weiss et al.
2004/0137612 A1  7/2004  Baksh et al.
2005/0019911 A1  1/2005  Gronthos et al.
2005/0158289 A1  7/2005  Simmons et al.
2005/0281790 A1  12/2005 Simmons et al.
2006/0008452 A1  1/2006  Simmons et al.
2006/0193840 A1  8/2006  Gronthos et al.
2006/0199263 A1  9/2006  Auger et al.
2006/0286077 A1  12/2006 Gronthos et al.

FOREIGN PATENT DOCUMENTS

| WO | WO-01/11011 A2    | 2/2001  |
|----|-------------------|---------|
| WO | WO-02/086104 A1   | 10/2002 |
| WO | WO-2004/072273 A1 | 8/2004  |
| WO | WO-2005/001076 A2 | 1/2005  |
| WO | WO-2005/085428 A1 | 9/2005  |
| WO | WO-2007/071048 A1 | 6/2007  |
| WO | WO-2007/099534 A2 | 9/2007  |
| WO | WO-2007/128115 A1 | 11/2007 |

OTHER PUBLICATIONS

Romanov et al 2003, on line Oct. 2002; Stem Cells 21-105-110.*
Shi et al 2003, J. Bone and Mineral Res. 18:696-704.*
Meyer et al. (Biochimica et Biophysica Acta. 1983; 755: 376-387).*
Romanov et al. (Stem Cells. 2003; 21: 105-110).*
Aubin, "Bone stem cells," J Cell Biochem Suppl. 30-31:73-82 (1998).
Beckstead et al., "Enzyme histochemistry on bone marrow biopsies: reactions useful in the differential diagnosis of leukemia and lymphoma applied to 2-micron plastic sections," Blood. 55(3):386-394 (1980).
Beckstead et al., "Enzyme histochemistry and immunohistochemistry on biopsy specimens of pathologic human bone marrow," Blood. 57(6):1088-1098 (1981).
Bianco et al., "Uno, nessuno e centomila: searching for the identity of mesodermal progenitors," Experimental Cell Res. 251:257-263 (1999).
Can et al., "Concise review: human umbilical cord stroma with regard to the source of fetus-derived stem cells," Stem Cells. 25:2886-2895 (2007).
Canfield et al., Osteogenic Potential of Vascular Pericytes. *Bone Engineering*. JE Davies, 143-151 (2000).
Caplan, "Mesenchymal stem cells," J Orthop Res. 9(5):641-650 (1991).
Chacko et al., Architecture of distended and nondistended human umbilical cord tissues, with special reference to the arteries and veins. *Contributions to Embryology*. Carnegie Institution of Washington publication, 135-150 (1954).
Challier et al., "Mixed culture of pericytes and endothelial cells from fetal microvessels of the human placenta," Cell Mol Biol. 41:233-241 (1995).

(Continued)

*Primary Examiner* — Scott Long
(74) *Attorney, Agent, or Firm* — Clark & Elbing LLP

(57) ABSTRACT

Human progenitor cells are extracted from perivascular tissue of human umbilical cord. The progenitor cell population proliferates rapidly, and harbors osteogenic progenitor cells and MHC−/− progenitor cells, and is useful to grow and repair human tissues including bone.

20 Claims, 18 Drawing Sheets

(56) References Cited

OTHER PUBLICATIONS

Conget et al., "Phenotypical and functional properties of human bone marrow mesenchymal progenitor cells," J Cell Physiol. 181:67-73 (1999).
Declaration under rule 132 of John E. Davies in U.S. Appl. No. 10/961,919, dated Feb. 20, 2007 (22 pages).
Etherington, "Proteinases in connective tissue breakdown," Ciba Found Symp. 75:87-103 (1979) (Abstract Only) (1 page).
Farias et al., "Human umbilical cord stromal stem cell express CD10 and exert contractile properties," Placenta. 32:86-95 (2011).
Friedenstein et al., "Fibroblast precursors in normal and irradiated mouse hematopoietic organs," Exp Hematol. 4:267-274 (1976).
Friedman et al., "Umbilical cord mesenchymal stem cells: adjuvants for human cell transplantation," Biol Blood Marrow Transplant. 13:1477-1486 (2007).
Gronthos et al., "Postnatal human dental pulp stem cells (DPSCs) in vitro and in vivo," Proc Natl Acad Sci USA. 97(25):13625-13630 (2000).
Haynesworth et al., "Cell-based tissue engineering therapies: the influence of whole body physiology," Adv Drug Deliv Rev. 33:3-14 (1998).
Hu et al., "Abundant progenitor cells in the adventitia contribute to atherosclerosis of vein grafts in ApoE-deficient Mice," J Clin Invest. 113(9):1258-1265 (2004).
Ivarsson et al., "Recruitment of type I collagen producing cells from the microvasculature in vitro," Exp Cell Res. 229:336-349 (1996).
Karahuseyinoglu et al., "Functional structure of adipocytes differentiated from human umbilical cord stroma-derived stem cells," Stem Cells. 26:682-691 (2008).
Kogler et al., "A new human somatic stem cell from placental cord blood with intrinsic pluripotent differentiation potential," J Exp Med. 200:123-135 (2004).
Kulkarni et al., "Absence of Wharton's jelly around the umbilical arteries," Indian J Pediatr. 74:787-789 (2007).
Levy et al., "Osteoprogenitor cells of mature human skeletal muscle tissue: an in vitro study," Bone. 29:317-322 (2001).
Minguell et al., "Mesenchymal stem cells," Exp Biol Med. 226(6):507-520 (2001).
Mitchell et al., "Matrix cells from Wharton's jelly forms neurons and glia," Stem Cells. 21:50-60 (2003).
Nanaev et al., "Stromal differentiation and architecture of the human umbilical cord," Placenta. 18:53-64 (1997).
Naughton et al., "Cells isolated from Wharton's jelly of the human umbilical cord develop a cartilage phenotype when treated with TGF beta in vitro," Faseb Journal. 11:A19 (1997) (Abstract Only).
Parry, "Some electron microscope observations on the mesenchymal structures of full-term umbilical cord," J Anat. 107:505-518 (1970).
Pennati, "Biomechanical properties of the human umbilical cord," Biorheology. 38:355-366 (2001).
Pereda et al., "New advances in human embryology: morphofunctional relationship between the embryo and the yolk sac," Medical Electron Micropsc. 32:67-78 (1999).
Romanov et al., "Searching for alternative sources of postnatal human mesenchymal stem cells: candidate MSC-like cells from umbilical cord," Stem Cells. 21:105-110 (2003).
Sarugaser et al., "Human umbilical cord Wharton's jelly as a source of mesenchymal progenitors capable of expressing a functional osteogenic phenotype," Podium Presentation—Tissue Engineering Society International Orlando, FL (2003).
Sarugaser et al., "Human umbilical cord perivascular cells as a source of mesenchymal progenitors capable of expressing a functional osteogenic phenotype," Poster Presentation—World Biomaterials Congress, Sydney, NSW, Australia (2004).
Sarugaser et al., "Human umbilical cord perivascular (HUCPV) cells: a source of cells for allogeneic cell based therapies," Podium Presentation—European Tissue Engineering Society, Lausanne, Switzerland (2004).
Sarugaser et al., "Human umbilical cord perivascular (HUCPV) cells: a source of mesenchymal progenitors," Stem Cells. 23:220-229 (2005).
Sarugaser et al., "Human umbilical cord Wharton's jelly as a source of mesenchymal progenitors capable of expressing a functional osteogenic phenotype," Podium Presentation—Orthopaedic Research Society, San Francisco, CA (2003).
Sarugaser et al., "Human mesenchymal stem cells self-renew and differentiate according to a deterministic hierarchy," PLoS One. 4:E6498, 1-11 (2009).
Sartore et al., "Contribution of adventitial fibroblasts to neointima formation and vascular remodeling: from innocent bystander to active participant," Circ Res. 89:1111-1121 (2001).
Schoenberg et al., "Studies on connecting tissue. V. Fiber formation in Wharton's jelly," Lab Invest. 9:350-355 (1960).
Schugar et al., "High harvest yield, high expansion, and phenotype stability of CD146 mesenchymal stromal cells from whole primitive human umbilical cord tissue," J Biomed Biotechnol. 2009:789526 (2009) (19 Pages).
Sen et al., "Adipogenic potential of human adipose derived stromal cells from multiple donors is heterogeneous," J Cell Biochem. 81:312-319 (2001).
Shi et al., "Perivascular niche of postnatal mesenchymal stem cells in human bone marrow and dental pulp," J Bone Mineral Res. 18:696-704 (2003).
Stenmark et al., "Hypoxic activation of adventitial fibroblasts: role in vascular remodeling," Chest. 122:326-334 (2002).
Takechi et al., "Ultrastructural and immunohistochemical studies of Wharton's Jelly umbilical cord cells," Placenta. 14:235-245 (1993).
Tuchmann-Duplessis et al., First week of development. *Illustrated human embryology*. Springer-Verlag, 14-61 (1972).
Wharton, *Adenographia*. Oxford Univ. Press, 242-248 (1996).
Weiss, *Histology: cell and tissue biology*. Elsevier Biomedical, 997-998 (1983).
Weiss et al., "Human umbilical cord matrix stem cells: preliminary characterizations and effect of transplantation in a rodent model of Parkinson's disease," Stem Cells. 24:781-792 (2006); and Supplemental Tables and Figures from web Edition (17 pages).
Zebardast et al., "Human umbilical cord perivascular cells (HUCPVC): A mesenchymal cell source for dermal wound healing," Organogenesis. 6:197-203 (2010).
European Search Report for European Patent Application No. EP 10173753.4, dated Feb. 2, 2011 (3 pages).

\* cited by examiner

PROGENITOR CELLS FROM WHARTON'S JELLY OF HUMAN UMBILICAL CORD

CROSS-REFERENCE TO RELATED APPLICATIONS

This application claims priority to, and is a continuation of, U.S. patent application Ser. No. 12/482,963, filed Jun. 11, 2009, which claims priority to U.S. patent application Ser. No. 10/961,919, filed Oct. 8, 2004, which is a continuation-in-part of International Application No. PCT/CA2004/000182, filed Feb. 10, 2004, which claims benefit to U.S. Provisional Application No. 60/446,275, filed Feb. 11, 2003. Each of these applications are hereby incorporated by reference in their entirety.

FIELD OF INVENTION

This invention focuses on the harvesting of a population of rapidly proliferating human cells from the connective tissue of the umbilical cord (UC); the culture of such cells in osteogenic, chondrogenic, adipogenic and myogenic conditions; the demonstration of a high percentage of cells within these populations that are immunologically incompetent, as shown by their lack of cell surface histocompatibility antigens; and the ability of these cells to be used as a source of multipotent progenitor cells for various cell-based therapies.

BACKGROUND OF THE INVENTION

The UC is one of the first structures to form following gastrulation (formation of the three embryonic germ layers). As folding is initiated, the embryonic disc becomes connected, by the primitive midgut (embryonic origin) to the primitive yolk sac (extra-embryonic origin) via the vitelline and allantoic vessels which in turn develop to form the umbilical vessels (Haynesworth et al., 1998; Pereda and Motta, 2002; Tuchmann-Duplessis et al., 1972). These vessels are supported in, and surrounded by, what is generally considered a primitive mesenchymal tissue of primarily extra-embryonic derivation called Wharton's Jelly (WJ) (Weiss, 1983). From this early stage, the UC grows, during gestation, to become the 30-50 cm cord seen at birth. It can be expected therefore, that WJ contains not only the fibroblast-like, or myo-fibroblast-like cells which have been described in the literature (see below), but also populations of progenitor cells which can give rise to the cells of the expanding volume of WJ necessary to support the growth of the cord during embryonic and fetal development.

WJ was first described by Thomas Wharton, who published his treatise Adenographia in (1656) (Wharton T W. Adenographia. Translated by Freer S. (1996). Oxford, U.K.: Oxford University Press, 1656; 242-248). It has subsequently been defined as a gelatinous, loose mucous connective tissue composed of cells dispersed in an amorphous ground substance composed of proteoglycans, including hyaluronic acid (Schoenberg et al., 1960), and different types of collagens (Nanaev et al., 1997). The cells dispersed in the matrix have been described as "fibroblast-like" that are stellate in shape in collapsed cord and elongate in distended cord (Parry, 1970). Smooth muscle cells were initially observed within the matrix (Chacko and Reynolds, 1954), although this was disputed by Parry (1970) who described them as somewhat "unusual fibroblasts" which superficially resemble smooth muscle cells. Thereafter, little work had been done on characterizing these cells until 1993 when Takechi et al. (1993) performed immunohistochemical investigations on these cells. They described the cells as "fibroblast-like" that were "fusiform or stellate in shape with long cytoplasmic processes and a wavy network of collagen fibres in an amorphous ground substance" (Takechi et al., 1993). For the immunohistochemical staining, they used primary antibodies against actin and myosin (cytoplasmic contractile proteins), vimentin (characteristic of fibroblasts of embryonic mesenchyme origin) and desmin (specific to cells of myogenic origin) in order to determine which types of myosin are associated with the WJ fibroblasts. They observed high levels of chemically extractable actomyosin; and although fibroblasts contain cytoplasmic actomyosin, they do not stain for actin or myosin, whereas the WJ fibroblasts stained positively for both. Additionally, positive stains for both vimentin and desmin were observed leading to the conclusion that these modified fibroblasts in WJ were derived from primitive mesenchymal tissue (Takechi et al., 1993). A subsequent, more recent study by Nanaev et al. (1997) demonstrated five steps of differentiation of proliferating mesenchymal progenitor cells in pre-term cords. Their findings supported the suggestion that myofibroblasts exist within the WJ matrix. The immunohistochemical characterization of the cells of WJ, shows remarkable similarities to that of pericytes which are known to be a major source of osteogenic cells in bone morphogenesis and can also form bone nodules referred to as colony forming unit-osteoblasts (CFU-O) (Aubin, 1998) in culture (Canfield et al., 2000).

Recent publications have reported methods to harvest cells from UC, rather than UC blood. Mitchell et al. (Mitchell et al., 2003) describe a method in which they first remove and discard the umbilical vessels to harvest the remaining tissue. The latter, which will include both the remaining WJ (some of which will have been discarded with the vessels, since the umbilical vessels are entirely enveloped in WJ) and the amniotic epithelium, is then diced to produce small tissue fragments that are transferred to tissue culture plates. These tissue fragments are then used as primary explants from which cells migrate onto the culture substratum.

In another publication, Romanov et al. (2003) indicate they were successful in isolating mesenchymal stem cell-like cells from cord vasculature, although they also indicate their cultures do not contain cells from WJ. Specifically, they employ a single, 15 min, collagenase digestion from within the umbilical vein, which yields a mixed population of vascular endothelial and sub-endothelial cells. Romanov et al. show that sparse numbers of fibroblast-like cells appear from this cell harvest after 7 days.

Also, U.S. Pat. No. 5,919,702 describes a method of isolating "pre-chondrocytes" from the WJ of human UC, and their use to produce cartilage. Particularly, the method comprises slicing open a one inch section of cord longitudinally, dissecting away the blood vessels and 'casing', which are then discarded, and collecting the WJ into a sterile container where it was cut into 2-3 $mm^3$ sections for culturing. In a preferred method, cells are isolated by placing a 2-3 $mm^3$ section of the WJ on a glass slide on the bottom of a Petri dish, covering it with another slide, and culturing it for 10-12 days in order to allow the 'pre-chondrocytes' to migrate out to the culture dish surface.

It is an object of the present invention to provide a cell population comprising human progenitor cells.

It is another object of the present invention to provide a source from which human progenitor cells can be extracted.

It is a further object of the present invention to provide a method for the isolation of human progenitor cells.

It is a further object of the present invention to provide human osteoprogenitor cells useful for the production of bone tissue.

It is a further object of the present invention to provide human mesenchymal progenitor cells useful for the production of cartilage tissue, adipose tissue and muscle tissue.

It is a further object of the present invention to provide human immuno-incompetent progenitor cells useful therapeutically.

SUMMARY OF THE INVENTION

There has now been devised a procedure for extracting cells from Wharton's jelly of human umbilical cord, which yields a unique cell population characterized by rapid proliferation, the presence of osteoprogenitor and other human progenitor cells, including immuno-incompetent cells which display neither of the major histocompatibility markers (human leukocyte antigen (HLA) double negative). The cell population is a useful source of progenitor cells from which to grow bone and other connective tissues including cartilage, fat and muscle, and for autogenic and allogeneic transfer of progenitor cells to patients, for therapeutic purposes.

More particularly, and according to one aspect of the present invention, there is provided a Wharton's jelly extract, wherein the extract comprises human progenitor cells and is obtained by enzymatic digestion of the Wharton's jelly proximal to the vasculature of human umbilical cord, in a region usefully termed the perivascular zone of Wharton's jelly. The tissue within this perivascular zone, and from which the present progenitor cells are extracted, can also be referred to as perivascular tissue. The extraction procedure suitably results in an extract that is essentially free from cells of umbilical cord blood, epithelial cells or endothelial cells of the UC and cells derived from the vascular structure of the cord, where vascular structure is defined as the tunicae intima, media and adventia of arteriolar or venous vessels. The resultant extract is also distinct from other Wharton's jelly extracts isolated from the bulk Wharton's jelly tissue that has been separated from the vascular structures.

In accordance with another of its aspects, the present invention provides a method for obtaining a human progenitor cell, comprising the step of isolating the cell from the Wharton's jelly extract obtained in accordance with the invention.

In a related aspect, the present invention provides a cell population obtained by culturing of the cells present in the Wharton's jelly extract. In embodiments, there is provided a population of osteoprogenitor cells. In other embodiments, there is provided a population of immuno-incompetent progenitor cells.

In one embodiment, the extracted progenitor cell population is characterized as an adherent cell population obtained following culturing of the extracted cells under adherent conditions. In another embodiment, the extracted progenitor cell population is characterized as a non-adherent (or "post-adherent") (PA) cell population present within the supernatant fraction of extracted cells grown under adherent conditions. This PA fraction is derived by transferring the supernatant of the initially plated HUCPV cells into a new T-75 flask to allow the as yet non-adhered cells to attach to the culture surface. This process is repeated with this new T-75 flask, transferring its media into another new T-75 flaks in order to harvest any remaining PA cells. This PA cell population comprises, according to another aspect of the invention, a subpopulation of progenitor cells that, when cultured under adherent conditions, proliferates rapidly and forms bone nodules and fat cells spontaneously. This embodiment provides a means to increase the yield of adherent cells isolated from the enzymatic digest cell population.

Also provided by the present invention is a population of committed osteoprogenitor cells characterized by the property of differentiating into bone cells when cultured in the absence of supplements otherwise required for such differentiation.

In another of its aspects, the present invention provides a method for producing connective tissue, including bone tissue, cartilage tissue, adipose tissue and muscle tissue, which comprises the step of subjecting cells obtained from the Wharton's jelly extract to conditions conducive to differentiation of those cells into the desired connective tissue phenotype. In this respect, the invention further provides for the use of such cells in cell-based therapies including cell transplantation-mediated treatment of medical conditions, diseases and disorders.

More particularly and according to another aspect of the invention, there is provided a composition and the use thereof in tissue engineering, comprising progenitor cells in accordance with the invention or their differentiated progeny, and a carrier suitable for delivering such cells to the chosen tissue site.

These and other aspects of the invention will now be described in greater detail with reference being had to the accompanying drawings, in which:

DETAILED DESCRIPTION OF THE INVENTION

The present invention provides an extract of Wharton's jelly (WJ), as a source of a rapidly proliferating cell population comprising human progenitor cells including osteoprogenitor cells, as well as immuno-incompetent cells.

For purposes of this description, the extracted cell population can be referred to as human umbilical cord perivascular (HUCPV) cells. The HUCPV cell population constitutes a rich source of multipotent progenitor cells that are unique in their phenotype, particularly as revealed by the variety of cell subpopulations contained therein. Also for purposes of this description, the perivascular zone of the Wharton's jelly from which the present cells are extracted can be referred to as perivascular tissue.

As used herein, the term "progenitor cells" refers to cells that will differentiate under controlled and/or defined conditions into cells of a given phenotype. Thus, an osteoprogenitor cell is a progenitor cell that will commit to the osteoblast lineage, and ultimately form bone tissue when cultured under conditions established for such commitment and differentiation. A progenitor cell that is "immuno-incompetent" or "non-immunogenic" is a cell having a phenotype that is negative for surface antigens associated with class I and class II major histocompatibility complexes (MHC). Such a progenitor cell is also referred to herein as an HLA double negative.

Figure 16:
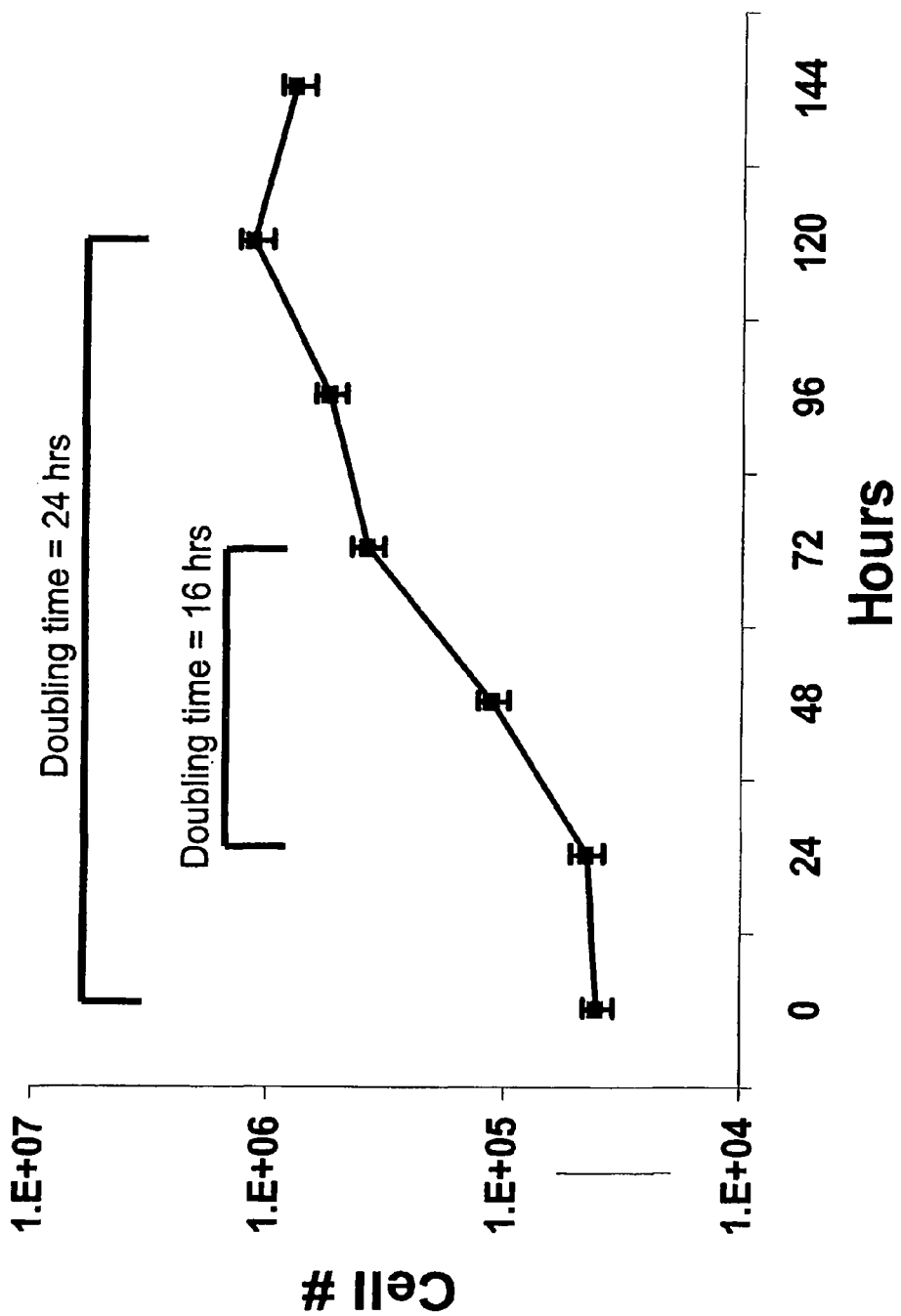
FIG. 16 shows proliferation of the perivascular WJ cells from 0-144 hours illustrating a normal growth curve with a lag phase from 0-24 hrs, log phase from 24-72 hours, and plateau phase from 72-120 hours. The doubling time during the entire culture period is 24 hours, while during log phase it is 16 hours.

The HUCPV cell population extracted from WJ is also characterized by "rapid proliferation", which refers to the rate at which the extracted cells will grow relative to other known progenitor cell populations, under conditions that are standard for progenitor cell expansion. As will be appreciated from the experimental results presented herein, and as shown in FIG. 16, the present progenitor cell population can double within at least about 25 hours and as quickly as 7-15 hours, and thus expands far more rapidly than other known osteoprogenitor cell populations and other progenitor cell populations extracted from WJ.

The cells and cell populations of the present invention can be obtained by extraction from WJ of human umbilical cord. Unlike the prior art, and in accordance with the present invention, such cells are extracted from the WJ that is associated with, i.e., proximal to, the exterior wall of the umbilical vasculature. The Wharton's jelly that is associated with or very near to the external surface of the cord vasculature lies within a region termed the perivascular zone, and typically remains associated with the vasculature when the vessels are excised from the cord, as is done for instance either to extract Wharton's jelly from the cord, or to extract the vessels from the cord and associated Wharton's jelly. It has remarkably been found that the Wharton's jelly within this perivascular zone, and which has typically been discarded in prior art practice, is a rich source of progenitor cells having the characteristics herein described. Accordingly, the present invention exploits the tissue from this perivascular zone of the Wharton's jelly as a source for useful human progenitor cells, termed HUCPV cells.

In embodiments, the HUCPV cell population is characterized by the presence of progenitor cells having many markers indicative of a functional mesenchymal (non-hematopoietic) phenotype, i.e., CD45−, CD34−, SH2+, SH3+, Thy−1+ and CD44+. Of particular significance, the population is characterized generally as harbouring cells that are positive for 3G5 antibody, which is a marker indicative of pericytes. The extracted cell population generally is a morphologically homogeneous fibroblastic cell population, which expresses alpha-actin, desmin, and vimentin, and provides a very useful source from which desired cell subpopulations can be obtained through manipulation of culturing conditions and selection based for instance on cell sorting principles and techniques.

To extract such perivascular cells from human umbilical cord, in a preferred embodiment, care is taken during the extraction process to avoid extracting cells of the umbilical cord blood, epithelial cells or endothelial cells of the UC, and cells derived from the vascular structure of the cord, where vascular structure is defined as the tunicae intima, media and adventia of arterial or venous vessels. Obtaining an extract that is essentially free of these unwanted cells can be achieved by careful flushing and washing of the umbilical cord prior to dissection, followed by careful dissection of the vessels from within the cord. The vessels can also be carefully pulled away from the surrounding cord tissue in which case the perivascular tissue is excised with the vessels. It will be appreciated that, with care being taken to avoid extracting these unwanted cells, they may still be present to a small extent in the resulting extract. This is acceptable provided they occur at a frequency too low to interfere with the observed results presented herein, i.e., observation of cell colonies derived from mesenchymal and specifically mesodermal origin, frequency and rapidity of formation of CFU-F, CFU-O and CFU-A, and characterization of HLA phenotypes observed in the cultured population.

The tissue that lies within the perivascular zone is the Wharton's jelly proximal to the external wall of the umbilical vasculature, and lies typically within a zone extending to about 3 mm from the external wall of the vessels. Suitably, the target extraction zone can lie within about 2 mm, e.g., about 1 mm from the external wall of any one of the three vessels. The extraction of WJ from this region can be readily achieved using the technique described in the examples. In this technique the vessels are used as a carrier for the WJ, and the vessels per se are used as the substrate from which the progenitor cells are extracted. Thus, in embodiments of the invention, cord vessels bearing a thin coating of perivascular tissue are excised either surgically or manually from fresh umbilical cord that has been washed thoroughly to remove essentially all cord blood contaminants. The vessels bearing the proximal perivascular tissue, or sections thereof, are then incubated at about 37° C. in an extraction medium such as phosphate buffered saline (PBS) containing an enzyme suitable for digesting the collagen matrix of the perivascular tissue in which the desired cells reside. For this purpose, digestion with a collagenase is suitable, at a concentration within the range from about 0.1 mg/mL to 10.0 mg/mL or more, e.g., 0.5 mg/mL. The enzyme type, concentration and incubation time can vary, and alternative extraction conditions can be determined readily simply by monitoring yield of cell phenotype and population under the chosen conditions. For instance, a higher collagenase concentration of 4 mg/mL (e.g., 1-4 mg/mL) is also suitable over a shorter digestion period of about 3 hours (e.g., 1-5 hours). During the extraction, the ends of the vessels are tied, or clipped, off and can be suspended above the extraction medium to avoid contamination by agents contained within the vessel. It will thus be appreciated that the present Wharton's jelly extract is essentially free from cord blood cells, umbilical cord epithelial cells, vessel endothelial cells and vessel smooth muscle cells.

Figure 21:
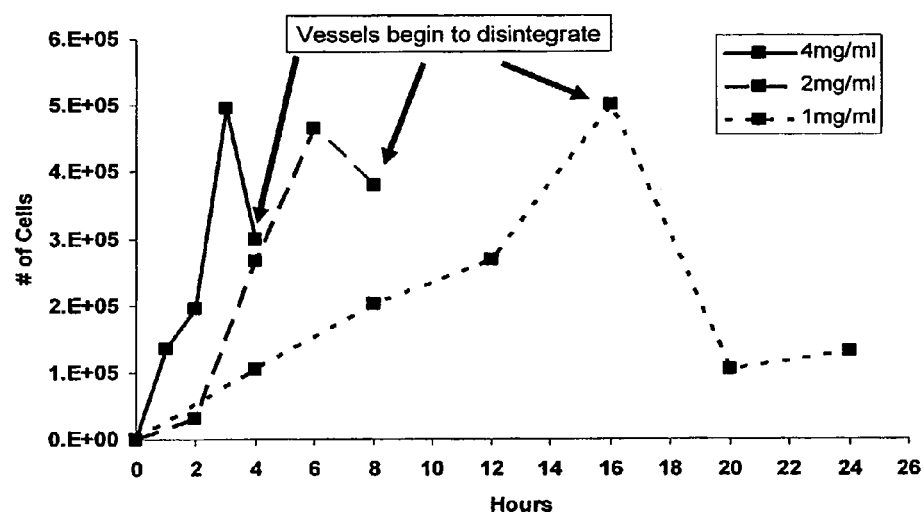
FIG. 21 shows the effects of collagenase concentration and digestion time on cell harvest.

Other digestive enzymes that can be used in the isolation procedure are 0.1 to 10 mg/ml hyaluronidase, 0.05 to 10 mg/ml trypsin as well as EDTA. The optimum collagenase concentration is 4 mg/ml for a digestion period of 3 hours, although a less expensive alternative is to use 0.5 mg/ml for 18-24 hours. Still other alternatives to collagenase concentrations are illustrated in FIG. 21. Desirably, digestion is halted at or before the vessels begin to degrade which, as shown in FIG. 21, occurs at different time points depending on the collagenase concentration.

After about 24 hours in the 0.5 mg/mL collagenase extraction medium, e.g., 12-36 hours, such as 18-24 hours, or after about 3 hours in the 4.0 mg/mL collagenase extraction medium, the vessels are removed, leaving a perivascular tissue extract that contains human progenitor cells. These cells are expanded under conditions standard for expansion of progenitor cells. The cells can, for instance, be selected on polystyrene to select for adherent cells, such as in polystyrene dishes or flasks and then maintained in a suitable culturing medium. In an embodiment of the invention, the extracted cells are cultured for expansion, with or without prior selection for adherent cells, under conditions of stirred suspension, as described for instance by Baksh et al in WO02/086104, the disclosure of which is incorporated herein by reference.

In a particular embodiment of the present invention, the extracted population of HUCPV cells is cultured under adherent conditions, and non-adherent cells resident in the supernatant are recovered for further culturing. These "post-adherent" cells are characterized as a subpopulation by a propensity to form bone nodules and fat cells spontaneously, and constitute a valuable embodiment of the present invention. Thus, in this respect, the present invention further provides an isolated population of progenitor cells extracted from perivascular tissue, the cells having the propensity to form at least one of several differentiated cell types including bone cells, cartilage cells, fat cells and muscle cells, wherein such progenitor cells constitute the non-adherent fraction of the HUCPV cells cultured under adherent conditions. Such cells are obtained by culturing the perivascular tissue-extracted HUCPV cells under adherent conditions, selecting the non-adherent cell population, and then culturing the non-adherent cell population under conditions useful to (1) expand said population or (2) to cause differentiation thereof into a desired cell phenotype. Culturing conditions useful therein are those already established for such expansion and differentiation, as exemplified herein.

It will also be appreciated that the present invention includes HUCPV subpopulations that are cultured and expanded under standard adherent culturing conditions. As is revealed herein, such adherent cell populations are known to comprise the immunoincompetent or non-immunogenic, progenitors, and mesenchymal progenitors, which constitute valuable embodiments of the present invention.

The cells present in the extract can, either directly or after their expansion, be sorted using established techniques to provide expandable subpopulations enriched for cells of a given phenotype. Thus, the present invention further provides perivascular tissue extracted cell populations that are enriched for multipotent mesenchymal progenitor cells, osteoprogenitor cells, cell populations that are enriched for immuno-incompetent progenitor cells, and cell populations that are enriched for multipotent and osteoprogenitor cells that are immuno-incompetent. Further, the cells can be enriched to select for only those that are positive for the pericyte marker 3G5, using antibody thereto, and to select only for those that are negative for either one or both of the MHC class I and class II markers. The cell population can also be enriched by selection against other surface markers, such as by depletion of those bearing CD45 to remove hematopoietic cells, for instance. Such enriched cell populations are valuable embodiments of the present invention.

Figure 17:
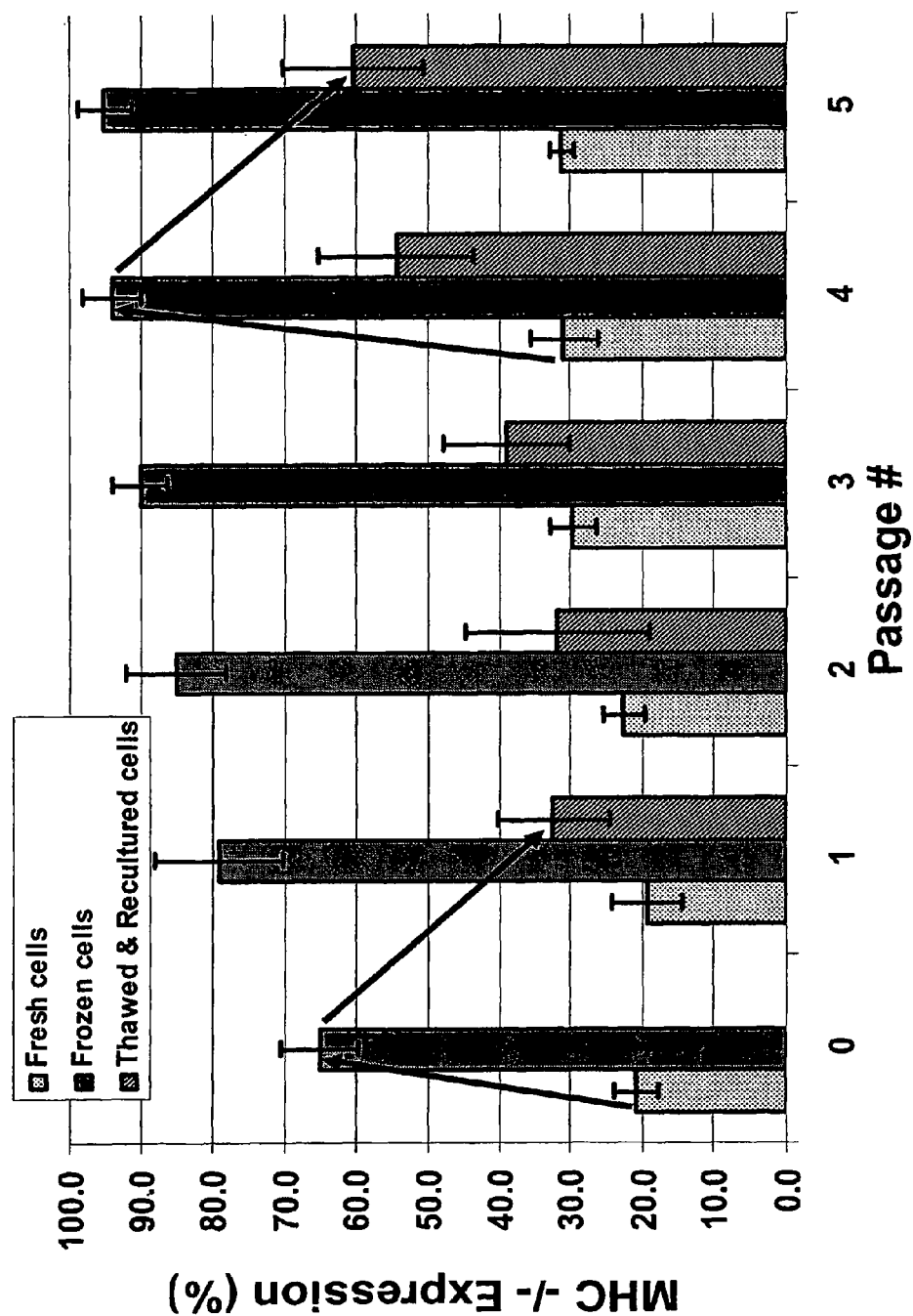
FIG. 17 shows major histocompatibility complex (MHC) expression of the WJ cells shown over 5 passages, the change in their expression due to free-thawing, and subsequent expression due to reculture.

As is revealed in FIG. 17, it has been found that the distribution of MHC markers within the progenitor cell population is altered by freeze-thawing. Upon passaging of fresh cells, the frequency of MHC double negative cells is relatively constant/marginally increased. However, it has been found, as noted in the examples herein, that the frequency of MHC double negative cells in the progenitor population is increased significantly in cells plated following freezing. Thus, in the present progenitor cell population, cells of the MHC double negative phenotype are further characterized by the propensity to increase in frequency following freezing. Such freezing is performed in the usual manner, by first preparing a cell aliquot, and then storing the cell preparation for the desired period. It will be appreciated that such cells can be stored for many years if desired.

In an embodiment, the present invention thus further provides a method for producing MHC double negative progenitor cells, by obtaining a perivascular tissue extract as herein described, or an MHC double negative-enriched fraction thereof, subjecting the extract or fraction thereof to freezing, and then culturing the frozen cells. The resulting cells as noted are potentially useful to induce tissue formation or repair in human subjects.

The cell populations obtained from the extract or from a suitably enriched fraction thereof, are useful either directly or following their expansion to provide differentiated cell populations. All of the procedures suitable for their fractionation and enrichment, and for their expansion are established in the prior art, and are exemplified herein. Expansion can proceed, for instance, in the presence of factors such as IL-3 and Stem Cell Factor, and similar agents known in the art. In one embodiment, the present cell population, and particularly the osteoprogenitor cells therein, are subjected to differentiation using conditions established for the growth of bone tissue therefrom. Remarkably, a subpopulation of osteoprogenitor cells that arise from the culturing of the present progenitor cell population, referred to as committed osteoprogenitors, have shown the ability to differentiate in the absence of osteogenic supplements. Alternatively, the osteoprogenitor cells are cultured in a medium supplemented with one or more agents that stimulate osteogenesis, such as dexamethasone. In addition, the progenitor cells can also be cultured with supplements suitable for stimulating differentiation into other mesenchymally-derived connective tissues (Caplan, 1991), including cartilage, muscle, tendon, adipose etc., all in accordance with standard practice in the art.

As a practical alternative to in vitro culturing of cells in the present cell population, it will be appreciated that the cells can be transplanted in vivo to induce the formation of a desired tissue directly within a patient. By this route, the in situ formation of bone is provided by implanting osteoprogenitor, for the benefit of patients suffering from various bone conditions, diseases and disorders, particularly including bone fracture and osteoporosis. Such therapies can also be applied to attenuating maladies of other connective tissues such as, but not limited to, cartilage, fat and muscle. The immuno-incompetent progenitor cells present in the cell population are particularly valuable in this respect, given the substantially reduced rejection response that can be expected following their implantation.

For use in transplantation, the present cells can be provided as a composition, further comprising a carrier useful for their delivery to the tissue site selected for engineering. The cells are presented in a dose effective for the intended effect. It is expected that an effective cell dose will lie in the range from $10^3$ to $10^7$ cells, e.g., $10^4$-$10^6$ such as $2\times10^5$ cells, per dose. The carrier selected for delivery of those cells can vary in composition, in accordance with procedures established for delivery of viable cells. In embodiments, the cells are exploited for purposes of bone tissue engineering. In one embodiment, the cells are presented with a carrier in the form of a scaffold material that serves to localize the cells as an implant at a bone site that is defective or fractured, or is surgically prepared to receive the implant. A variety of materials are suitable as carriers for this purpose. In a particular embodiment, the carrier is formed of resorbable material such as calcium phosphate, PLGA or mixtures thereof. Equivalent materials can be used, provided they allow for the cells to remain viable during formation and delivery of the composition, and are otherwise physiologically compatible at the implantation site.

Still other carriers suitable for delivery of the progenitor cells will include vehicles such as PBS and gels including hyaluronic acid, gelatin and the like with equivalents being useful provided they possess the pH and other properties required for cell viability.

It will also be appreciated that the present cells are useful as hosts for delivering gene expression products to the desired tissue site. That is, the present cells can in accordance with embodiments of the present invention, be engineered genetically to receive and express genes that upon expression yield products useful in the tissue repair process, such as the various growth factors which, in the case of bone tissue, can usefully include PTH, the BMPs, calcitonin, and the like. The cells can also be developed as transgenics for other purposes, such as by introduction of genes that alter the cell phenotype, to make it more robust, or more suitable to a given end-use.

Embodiments of the invention are described in the following examples.

Harvest of Progenitor Cells from Human Wharton's Jelly

The UCs were collected from full-term caesarian section infants immediately upon delivery at Sunnybrook & Women's College Hospital, Toronto, Canada. The UC was transferred by the surgeon into a sterile vessel containing medium (80% α-MEM, 20% antibiotics), and immediately transported to our laboratories at the Institute of Biomaterials & Biomedical Engineering, University of Toronto.

All procedures from this point on were performed aseptically in a biological safety cabinet. The UC was washed in Phosphate Buffered Saline (PBS) ($-Mg^{2+}$, $-Ca^{2-}$) three times to remove as much of the UC blood as possible, and transferred back into a container with medium. A length of approximately 6 cm of cord was cut with sterile scissors and placed onto a sterile cork dissection board. The remaining cord (30-45 cm) was returned to the medium-filled container and placed into an incubator at 37° C. The 6 cm section of cord was 'twisted' against its helix, and pinned at both ends to reveal a smooth and straight surface of the UC epithelium. Using fine scissors, the UC was cut approximately 1-2 mm deep along its length to reveal the WJ. Starting with each 'flap' of cut epithelium, the WJ was teased from its inner surface using the blunt edge of a scalpel, and the teased away epithelium (approximately 0.5 mm thick) was pinned down. This procedure resulted in the WJ being exposed, and with its three vessels embedded in it running straight from end to end rather than helically along its longitudinal axis. Care was taken to constantly bathe the section with 37° C. PBS. Isolating one of the ends of a vessel with forceps, it was teased away from the WJ along its length until it was free of the bulk of the WJ matrix. Alternatively, the middle of the vessel could be dissected from the matrix, held with tweezers, and teased from the matrix in each direction toward its ends. Once freed by either method, the vessel was surrounded with approximately 1-2 mm of the cell-bearing WJ matrix. The dissected vessel was then clipped at both ends with either a surgical clamp, mosquito clip or sutured to create a 'loop,' blocking the passage of fluid either into or out of the vessel. The 'loop' was immediately placed along with the scissors into a 50 ml tube containing a 0.5 mg/ml collagenase solution with PBS ($-Mg^{2+}$, $-Ca^{2+}$), and placed into an incubator at 37° C. The remaining two vessels were dissected in a similar fashion, looped, and also placed in the collagenase solution in the incubator. Subsequent to the removal of the vessels, strips of WJ, constituting perivascular tissue, could easily be dissected off the epithelium and placed into 50 ml tubes with the collagenase solution. The remaining epithelial layer was then disposed of in a biohazard waste container. The same protocol was used with the remaining 30-45 cm of UC, producing 15 to 25 tubes with either 'loops' or perivascular tissue strips.

Initiation of Wharton's Jelly Progenitor Cell Cultures

After 18-24 hours, the 'loops' were removed with the aid of their attached suspension clamp or suture and a pipette, and the remaining suspensions were then diluted 2-5 times with PBS and centrifuged at 1150 rpm for 5 minutes to obtain the cell fraction as a pellet at the bottom of the tube/s. After removal of the supernatant, the cells were resuspended in eight times volume of 4% $NH_4Cl$ for 5 minutes at room temperature in order to lyse any contaminating red blood cells. The suspensions were then centrifuged again at 1150 rpm for 5 minutes to isolate the cell fraction as a pellet, and the supernatant was removed. After counting the cells with the use of hemocytometer, they were plated directly onto T-75 $cm^2$ tissue culture polystyrene dishes, and allowed to incubate at 37° C. for 24-72 hours in order to allow the cells to attach to the polystyrene surface. The medium was then changed every two days.

The results detailed below have been reproduced using the procedure described above, but in which collagenase-based digestion proceeded either at 4 mg/mL for 3 hours, 2 mg/ml for six hours and at 1 mg/mL for 12 hours.

The attached cells were passaged using 0.1% trypsin solution after 7 days, at which point they exhibited 80-90% confluency, as observed by light microscopy, and there was evidence of 'mineralized' aggregate formation, as revealed under phase microscopy and indicated by expected changes in optical properties. Upon passage, cells were plated either in 35 mm tissue culture polystyrene dishes or 6 well plates at $4 \times 10^3$ cells/cm² in supplemented media (SM) (75% α-MEM or D-MEM, 15% FBS, 10% antibiotics) and treated with $10^{-8}$M Dex, 5 mM β-GP and 50 µg/ml ascorbic acid to test the osteogenic capacity of these cells. These plates were observed on days 2, 3, 4 and 5 of culture for CFU-O otherwise referred to as 'bone nodule' formation.

In order to test the chondrogenic capacity of these cells, $2 \times 10^5$ cells were centrifuged at 1150 rpm for 5 minutes in order to obtain the cells as a pellet. Once the supernatant was removed, the cells were maintained in SM supplemented with 10 ng/ml transforming growth factor-beta (TGF-β) (and optionally with $10^{-7}$M dexamethasone). The supplemented medium was replaced every two days, maintaining the cultures for 3-5 weeks, at which point they were harvested for histology (by fixation with 10% neutral formalin buffer (NFB)), embedded in paraffin, cut into 6 µm section, and stained for the presence of collagen II (antibody staining) and the presence of glycosaminoglycans (alcian blue staining). To assess the adipogenic differentiation capacity of the cells, they were initially cultured in 6-well plates in SM (with D-MEM), which was replaced every 2 days, until they reached 60% confluence. At that point the medium was replaced with the adipogenic induction medium (AIM) (88% D-MEM, 3% FBS, 33 µM Biotin, 17 µM Pantothenate, 5 µM PPAR-gamma, 100 nM Bovine insulin, 1 µM Dexamethasone, 200 µM Isobutyl methylxanthine and 10% antibiotics). The AIM was replaced every 2 days for 10 days at which point the cells were fixed in 10% NFB and stained with Oil Red O which stains the lipid vacuoles of adipocytes red. Finally, in order to assess the myogenic capacity of the cells, they were initially cultured in T-75 cm² tissue culture flasks in SM (with D-MEM) until they reached 80-90% confluence, at which point the medium was replaced with myogenic medium (MM) (75% D-MEM, 10% FBS, 10% Horse serum, 50 µM hydrocortisone and 10% antibiotics). The MM was replaced every 2 days. After 3-5 weeks in culture, the cells were removed from the culture surface (see sub-culture protocol), lysed in order to obtain their mRNA, and assessed by rtPCR for the presence of several myogenic genes, including: MyoG, MyoD1, Myf5, Myosin heavy chain, myogenin and desmin.

Another useful approach to obtaining the perivascular tissue-derived progenitor cell cultures has been adopted, using the following protocol:

1. Obtain sterile umbilical cord (UC) from caesarian-section patient and transport to biological safety cabinet in media (80% α-MEM, 20% antibiotics)
2. Wash the UC 3× in sterile 37° C. phosphate buffered saline (PBS)
3. Cut the UC into approximately 1-2 inch sections with a sharp pair of scissors
4. Wash each section of UC 2× in sterile 37° C. PBS to remove as much residual umbilical cord blood (UCB) as possible.
5. Isolate one of the UC sections on a dry sterile dish
6. Using two sets of forceps, grasp the epithelium approximately 2 mm apart, and pull away from each other, tearing the epithelium.
7. Grasping the epithelium along the length of the UC section, continue to tear the epithelium away, exposing the WJ underneath
8. Similarly to step 6, continue tearing the epithelium away in 'strips' until approximately half of the epithelium has been torn away.
9. The umbilical vessels should be clearly visible through the WJ, and the ends loose on the cut edges of the UC section.
10. By grasping a remaining part of the epithelium with one set of forceps, and the end of a vessel with the other, the vessel can be 'pulled' from the bulk WJ with its surrounding perivascular tissue (PVT).
11. This process is repeated with each vessel, until all three are free of the underlying WJ matrix.
12. Once released, each vessel is placed into 37° C. PBS.
13. Steps 5-12 are repeated with each section of UC until all the vessels have been isolated in a sterile 37° C. PBS-filled beaker.
14. Then, by placing each vessel individually on a clean, sterile surface, the ends can be ligated together with a suture using a double knot into a 'loop'
15. Once all of the vessels have been ligated into loops, the loops are placed into a 0.5 mg/ml collagenase solution in a sterile 50 ml tube
16. The 50 ml tube is placed into a rotator in a 37° C., 5% $CO_2$ incubator overnight.
17. The following day, the collagenase is inactivated with 1 ml fetal bovine serum (FBS), and the loops removed from the suspension.
18. The remaining suspension is diluted with PBS, centrifuged at 1150 rpm for 5 minutes, and the supernatant removed.
19. The pellet is then resuspended in 8 times volume of 4% $NH_4Cl$ for 5 minutes at room temperature to lyse all contaminating red blood cells, then centrifuged at 1150 rpm for 5 minutes, and the supernatant removed.
20. The cells remaining in the pellet are resuspended in supplemented media (SM) (75% α-MEM, 15% FBS, 20% antibiotics), and aliquot is counted on a hemocytometer.
21. The cell suspension is then plated onto a T-75 tissue-culture polystyrene flask, and allowed to proliferate.
22. After 2 days, the supernatant from the flask is transferred to a new T-75 flask in order to harvest the post adherent"" (PA) cells.
23. After 2 days, the supernatant from the first PA flask is transferred to a new T-75 flask in order to harvest any remaining PA cells.
24. The SM is replaced in all three T-75 flasks every 2 days until the cells reach sub-confluence (1-2 weeks), at which point they are sub-cultured (passaged).

Progenitor Assays

Cell Proliferation Assay

During the weekly passage procedure (occurring every 6 days), aliquots of $3 \times 10^4$ cells were plated into each well of 24 6-well tissue culture polystyrene plates. On days 1, 2, 3, 4, 5 and 6 days of culture, four of the 6-well plates were passaged and the cells were counted. The exponential expansion of these cells was plotted, and the mean doubling time for the cells in these cultures was calculated. Results are shown in FIG. 16. It will be noted that the doubling time for the PVWJ cell culture is about 24 hours across the entire culturing period. During the log phase, the doubling time is a remarkable 16 hours. This compares with literature reported doubling times of about 33-36 hours for bone marrow mesenchymal cells (Conget and Minguell, 1999), and about 3.2 days for mesenchymal stem cells derived from adipose tissue (Sen et al., 2001). For observation of proliferation with successive passaging, $3 \times 10^5$ cells were plated into 4 T-75 flasks (n=4) and fed with SM which was replaced every 2 days. After 6 days of culture the cells were subcultured (see subculture protocol above), and counted with the use of a hemocytometer. Aliquot of $3 \times 10^5$ cells were seeded into 4 new T-75 flasks, cultured for 6 days, and the process of counting was repeated. This process was repeated from P0 through P9 for 4 cord samples.

Figure 18:
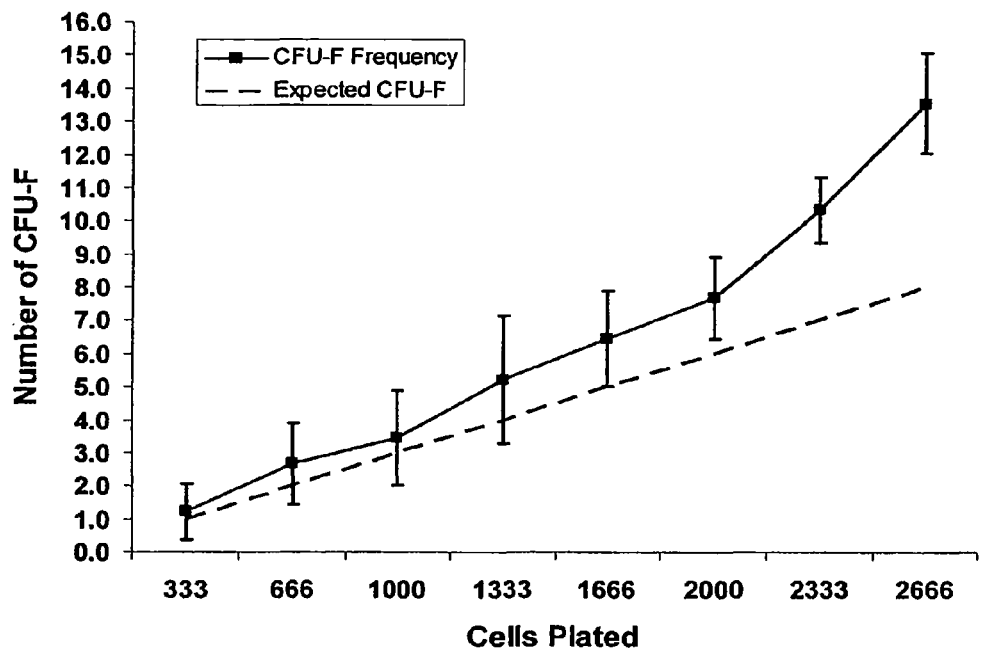
FIG. 18 shows the CFU-F frequency of HUCPV cells.
Figure 19:
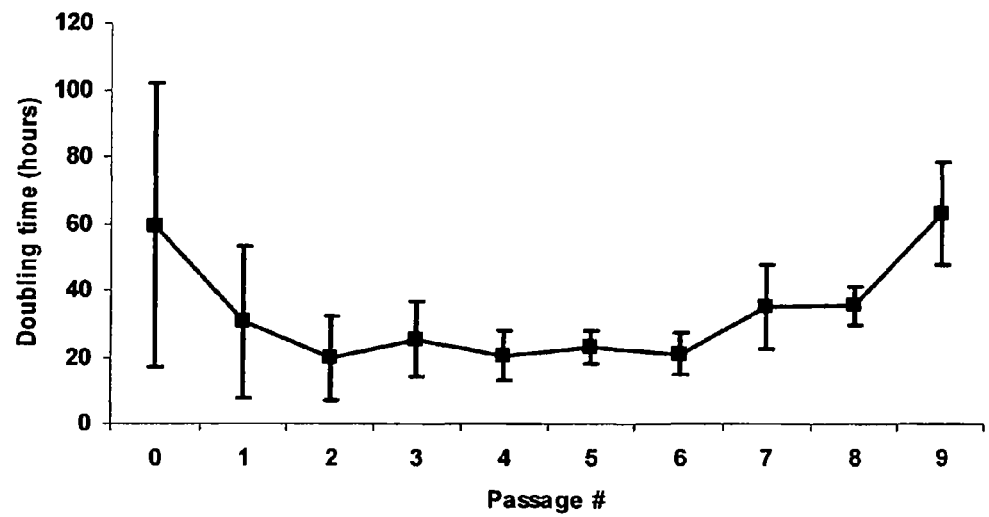
FIG. 19 shows the doubling time of HUCPV cells from P0 through P9. HUCPV cells demonstrate a relatively stable and rapid doubling time of 20 hours from P2 to P8.
Figure 20:
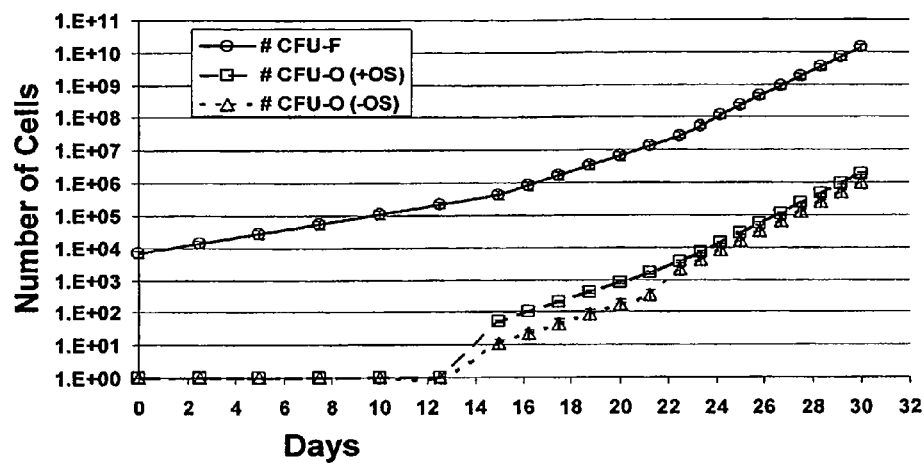
FIG. 20 shows the proliferation of HUCPV cells demonstrating that $>10^{14}$ cells can be derived within 30 days of culture. With this rapid expansion, 1,000 therapeutic doses (TDs) can be generated within 24 days of culture.

FIG. 18 illustrates the CFU-F frequency of HUCPV cells. The frequency of 1:300 is significantly higher than that observed for other mesenchymal progenitor sources including neonatal BM ($1:10^4$) (Caplan, 1991), and umbilical cord blood-derived "unrestricted somatic stem cells" (USSCs) (Kogler et al., 2004) which occur at a frequency of $1:2 \times 10^8$. FIG. 19 illustrates the proliferation rate of HUCPV cells with successive passaging. The initial doubling time of 60 hours at P0 drops to 38 hours at P1, which drops and maintains itself at 20 hours from P2-P8. The cells begin to enter senescence thereafter and their proliferation rate begins to drop rapidly. Interestingly, when observed during the first 30 days of culture (FIG. 20), HUCPV cells derive $2 \times 10^{10}$ cells within 30 days. As one therapeutic dose (TD) is defined as $2 \times 10^5$ cells (Horwitz et al, 1999) LHorwitz E M, Prockop D J, Fitzpatrick L A, Koo W W, Gordon P L, Neel M et al. Transplantability and therapeutic effects of bone marrow-derived mesenchymal cells in children with osteogenesis imperfecta. Nat Med 1999; 5:309-313.), HUCPV cells can derive 1 TD within 10 days of culture, and 1,000 TDs within 24 days of culture.

Figure 15:
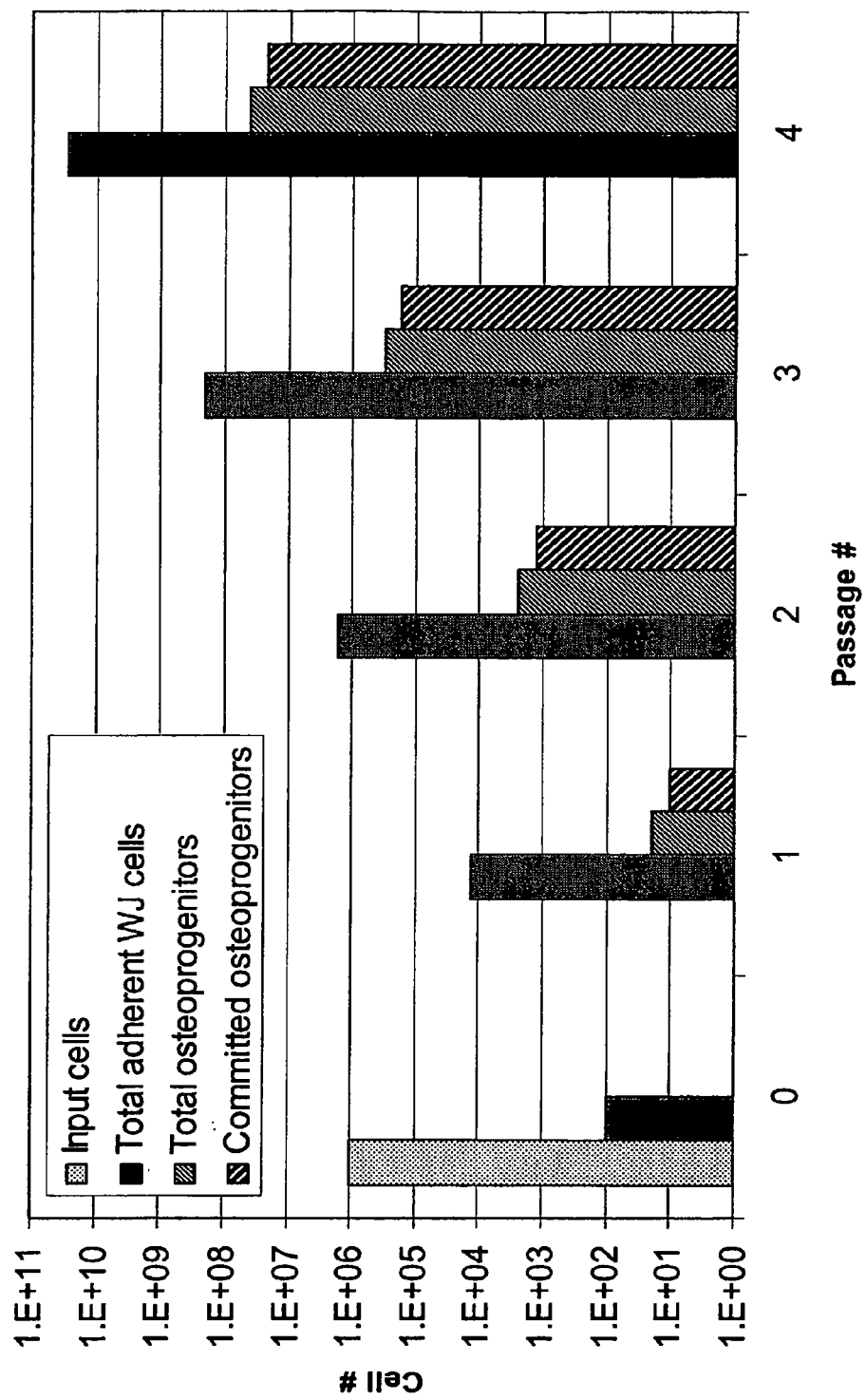
FIG. 15 shows the potential expansion of the adherent perivascular WJ population in relation to the expansion of the committed osteoprogenitor subpopulation and total osteoprogenitor subpopulation.

As shown in FIG. 15, the perivascular tissue-derived progenitors comprise different sub-populations of progenitor cells. Within this population, there are the so-called "committed" osteoprogenitor cells characterized by an ability to form bone nodules, as shown herein, in the absence of the culturing supplements normally required to induce such differentiation, such as culturing in the presence of dexamethasone. These committed osteoprogenitors thus differentiate spontaneously to form bone nodules. Also within the progenitor population are osteogenic cells that can be induced to form bone nodules, when cultured in the presence of the required factors, such as dexamethasone, β-glycerophosphate and ascorbic acid. Thus, the "total osteogenic" sub population graphed in FIG. 15 includes a "committed osteogenic progenitor" population, as well as an "uncommitted osteogenic progenitor" population, and reveals the total number of cells that can be induced to differentiate along the osteogenic differentiation pathway. The actual ratio between the "committed" and "uncommitted" population is approximately 1:1, and so the ratio between the "total osteogenic progenitor" population and the "committed osteogenic progenitor" population is about 2:1. Analysis of the bone forming properties of the progenitors was performed as noted below. Chondrogenic, adipogenic and myogenic differentiation of the cells has also been observed. Although osteogenic and occasional adipogenic differentiation has been observed spontaneously, the other phenotypes were only observed when cultured under specific induction conditions for the respective phenotype.

Serial Dilution and CFU-F Assays

Dilutions of $1 \times 10^5$, $5 \times 10^4$, $2.5 \times 10^4$, $1 \times 10^4$, $5 \times 10^3$, $1 \times 10^3$, HUCPV cells were seeded onto 6-well tissue culture plates (Falcon#353046) and fed every two days with SM. The number of colonies, comprising >16 cells, were counted in each well on day 10 of culture, and confirmed on day 14. CFU-F frequency, the average number of cells required to produce one colony, was consequently determined to be 1 CFU-F/300 HUCPV cells plated. Based on this frequency, the unit volume required to provide 300 HUCPV cells (done in triplicate from each of 3 cords) was calculated, and 8 incremental unit volumes of HUCPV cells were seeded into individual wells on 6-well plates. Again, colonies comprising >16 cells (CFU-Fs) were counted on day 10 of culture to assay CFU-F frequency with incremental seeding.

CFU-O Assay

During the weekly passage procedure, aliquots of test cell populations were directly plated on tissue-culture polystyrene in bone forming medium containing 75% α-MEM, 15% FBS (StemCell Batch #: S13E40), 10% antibiotic stock solution containing penicillin G (167 units/ml), gentamicin (50 μg/ml) and amphotericin B (0.3 μg/ml), and Dex ($10^{-8}$M), β-glycerophosphate (5 mM) and L-ascorbic acid (50 ug/ml), at a cell seeding density of $1 \times 10^4$ cells/cm$^2$. Cultures were re-fed every two days for a period of 12 days. The cultures were maintained until mineralized nodular areas, detected as bone nodules, were observed (usually 3 days) at which point the cultures were re-fed with tetracycline containing medium at the last culture re-feed, then fixed in Karnovsky's fixative and prepared for analysis. A Leitz Aristoplan microscope (Esselte Leitz GmbH & Co KG, Stuttgart, Germany) was used to visualize the tetracycline labelled cultures under phase contrast as well as UV fluorescence and a Hitachi S-2000 scanning electron microscope at an accelerating voltage of 15 kV was used to generate images to demonstrate the presence of morphologically identifiable bone matrix.

CFU-C Assay

In order to test the chondrogenic capacity of these cells, $2 \times 10^5$ cells were centrifuged at 1150 rpm for 5 minutes in order to obtain the cells as a pellet. Once the supernatant was removed, the cells were maintained in SM supplemented with 10 ng/ml transforming growth factor-beta (TGF-β) (and optionally with $10^{-7}$M dexamethasone). The supplemented medium was replaced every two days, maintaining the cultures for 3-5 weeks, at which point they were harvested for histology (by fixation with 10% neutral formalin buffer (NFB)), embedded in paraffin, cut into 6 μm section, and stained for the presence of collagen II (antibody staining) and the presence of glycosaminoglycans (alcian blue staining). Staining confirmed the formation of chondrocytes under induction conditions.

CFU-A Assay

To assess the adipogenic differentiation capacity of the cells, they were initially cultured in 6-well plates in SM (with D-MEM), which was replaced every 2 days, until they reached 60% confluence. At that point the medium was replaced with the adipogenic induction medium (AIM) (88% D-MEM, 3% FBS, 33 μM Biotin, 17 μM Pantothenate, 5 μM PPAR-gamma, 100 nM Bovine insulin, 1 μM Dexamethasone, 200 μM Isobutyl methylxanthine and 10% antibiotics). The AIM was replaced every 2 days for 10 days at which point the cells were fixed in 10% NFB and stained with Oil Red O which stains the lipid vacuoles of adipocytes red. Staining confirmed the formation of adipocytes, not only under induction conditions, but also in their absence, i.e., spontaneously CFU-M Assay In order to assess the myogenic capacity of the cells, they were initially cultured in T-75 cm$^2$ tissue culture flasks in SM (with D-MEM) until they reached 80-90% confluence, at which point the medium was replaced with myogenic medium (MM) (75% D-MEM, 10% FBS, 10% Horse serum, 50 μM hydrocortisone and 10% antibiotics). The MM was replaced every 2 days. After 3-5 weeks in culture, the cells were removed from the culture surface (see subculture protocol), lysed in order to obtain their mRNA, and assessed by rtPCR for the presence of several myogenic genes, including: MyoG, MyoD1, Myf5, Myosin heavy chain, myogenin and desmin. Results confirmed the presence of myocytes under these induction conditions.

Data Analysis

Tetracycline Stain

Tetracycline (9 μg/ml) was added to the cultures prior to termination. At termination, the cells were fixed in Karnovsky's fixative overnight and then viewed by UV-excited fluorescence imaging for tetracycline labeling of the mineral component of the nodular areas.

Scanning Electron Microscopy (SEM)

Representative samples of CFU-O cultures were prepared for SEM by first placing them in 70%, 80%, 90% and 95% ethanol for 1 hour, followed by immersion in 100% ethanol for 3 hours. They were then critical point dried. A layer of gold approximately 3 nm layer was sputter coated with a Polaron SC515 SEM Coating System onto the specimens, which were then examined at various magnifications in a Hitachi S-2000 scanning electron microscope at an accelerating voltage of 15 kV. The images generated are used to demonstrate the presence of morphologically identifiable bone matrix.

Flow Cytometry for HLA-Typing

Test cell populations of >1×10$^5$ cells were washed in PBS containing 2% FBS (StemCell Batch #: S13E40) and re-suspended in PBS+2% FBS with saturating concentrations (1:100 dilution) of the following conjugated mouse IgG1 HLA-A,B,C-PE and HLA-DR,DP,DQ-FITC for 30 minutes at 4° C. The cell suspension was washed twice with PBS+2% FBS, stained with 1 μg/ml7-AAD (BD Biosciences) and re-suspended in PBS+2% FBS for analysis on a flow cytometer (XL, Beckman-Coulter, Miami, Fla.) using the ExpoADCXL4 software (Beckman-Coulter). Positive staining was defined as the emission of a fluorescence signal that exceeded levels obtained by >99% of cells from the control population stained with matched isotype antibodies (FITC- and PE-conjugated mouse IgG1,κ monoclonal isotype standards, BD Biosciences). For each sample, at least 10,000 list mode events were collected. All plots were generated in EXPO 32 ADC Analysis software.

In addition to HLA typing, the HUCPV cell population was also assessed for other markers, with the following results:

| Marker | Expression |
|---|---|
| CD105 (SH2) | ++ |
| CD73 (SH3) | ++ |
| CD90 (Thy1) | ++ |
| CD44 | ++ |
| CD117 (c-kit) | 15%+ |
| MHC I | 75%+ |
| MHC II | − |
| CD106 (VCAM1) | − |
| STRO1 | − |
| CD123 (IL-3) | − |
| SSEA-4 | − |
| Oct-4 | − |
| HLA-G | − |
| CD34 | − |
| CD235a (Glycophorin A) | − |
| CD45 | − |

Results

Light Micrographs of Bone Nodule Colonies

Figure 1:
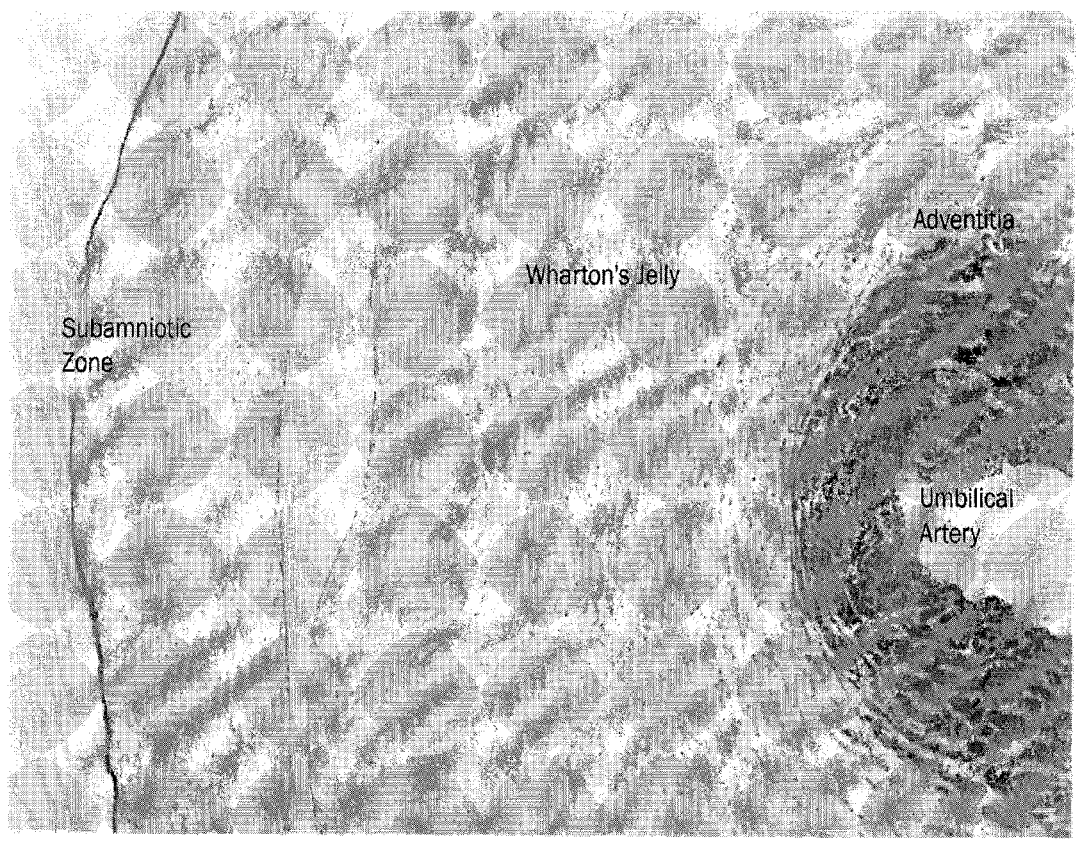
FIG. 1 is a light micrograph representing the three distinct zones of tissue represented in the human UC.
Figure 2:
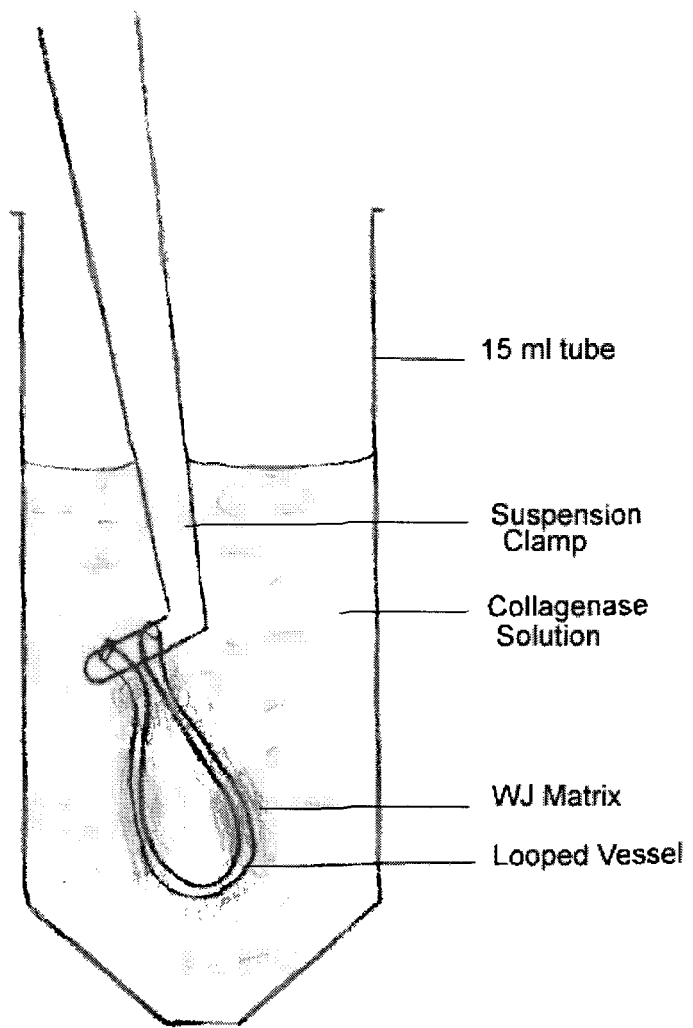
FIG. 2 is a representative illustration of the looped vessel in the collagenase solution.
Figure 3:
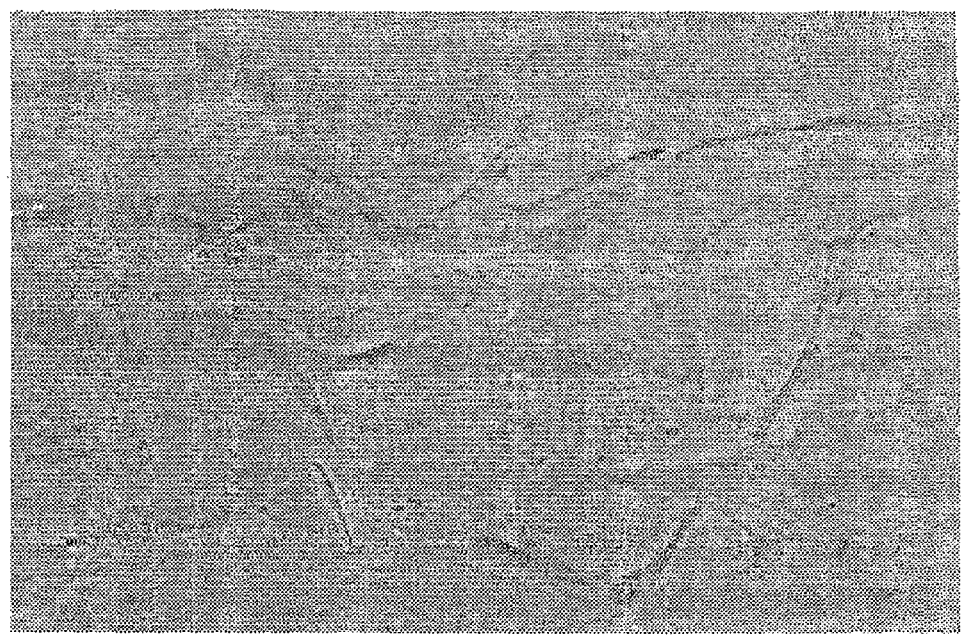
FIG. 3 is a light micrograph of the cells isolated from the WJ that have attached to the polystyrene tissue culture surface.
Figure 4:
FIG. 4 is a light micrograph illustrating the initial formation of a CFU-O.
Figure 5:
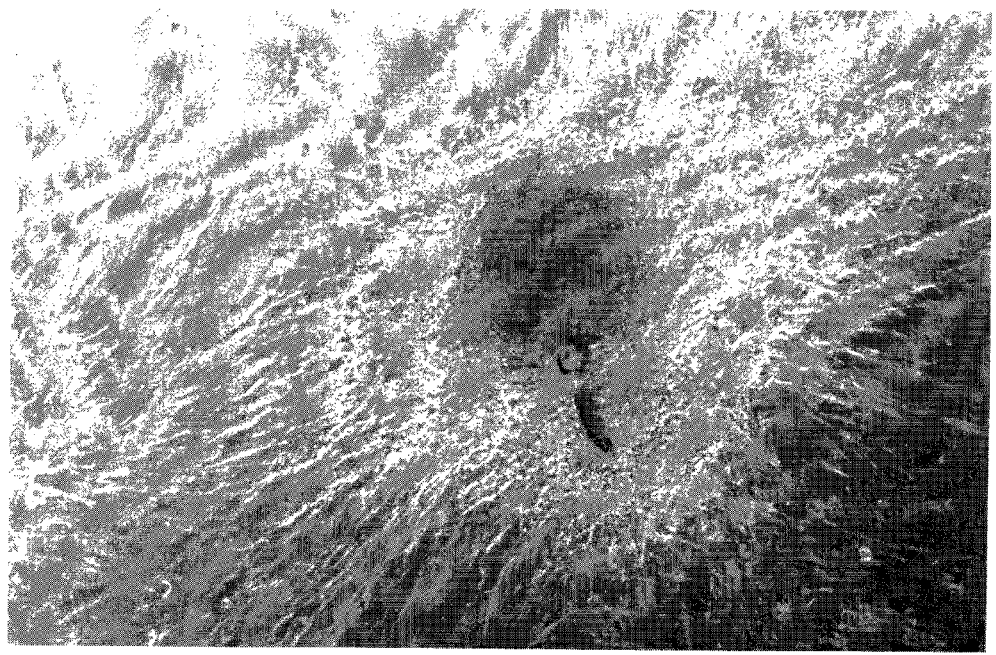
FIG. 5 is a light micrograph illustrating a mature CFU-O.

FIGS. 3, 4 and 5 illustrate CFU-O's that were present in the cultures on day 3 and day 5. They demonstrated the confluent layer of "fibroblast-like" cells surrounding a nodular area represented by an 'aggregation' of polygonal cells that were producing the bone-matrix. These CFU-O's were observed in both the Dex (+) and Dex (−) cultures, and displayed similar morphology over successive passages.

Tetracycline Labeling of CFU-O Cultures

Figure 6:
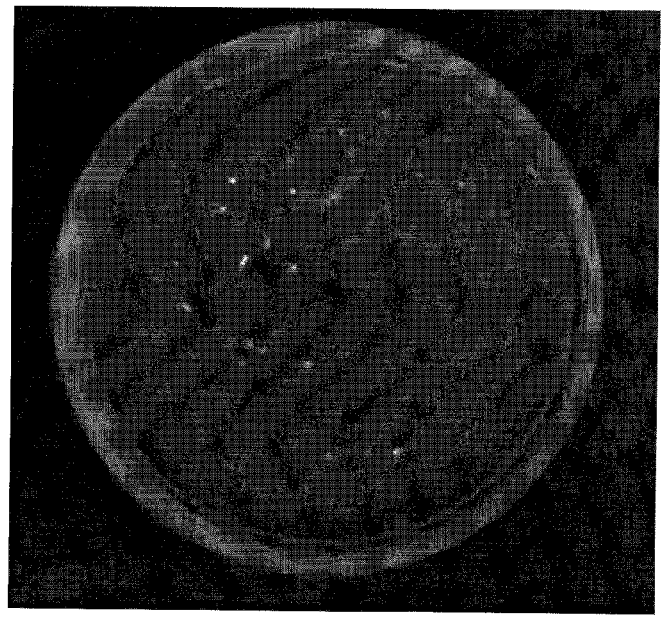
FIG. 6 demonstrates tetracycline-labeled CFU-O's under UV fluorescence on a 35 mm polystyrene tissue culture dish.
Figure 7:
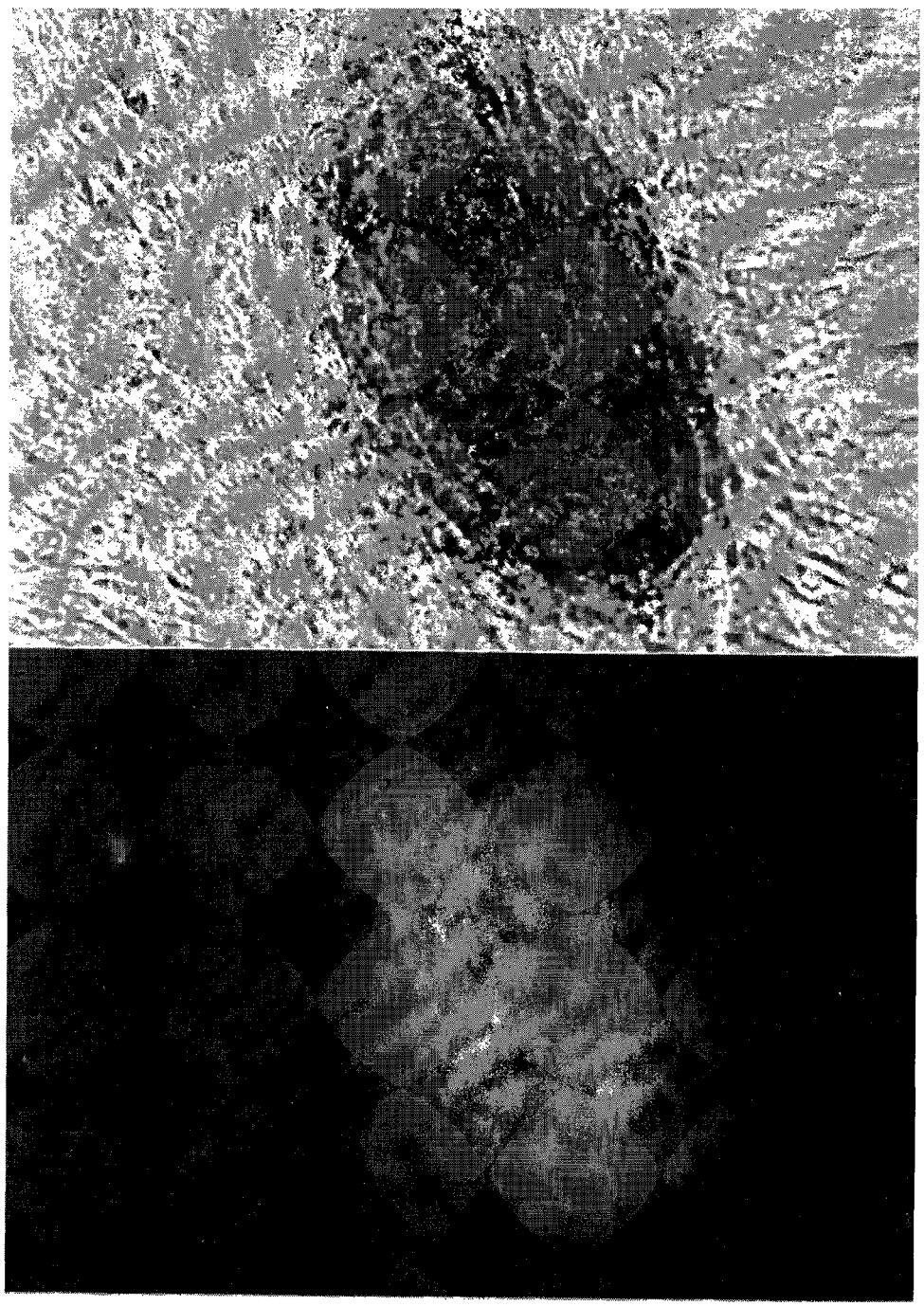
FIG. 7 illustrates side by side a phase-contrast light micrograph and a fluorescence micrograph of the same tetracycline-labeled CFU-O.
Figure 8:
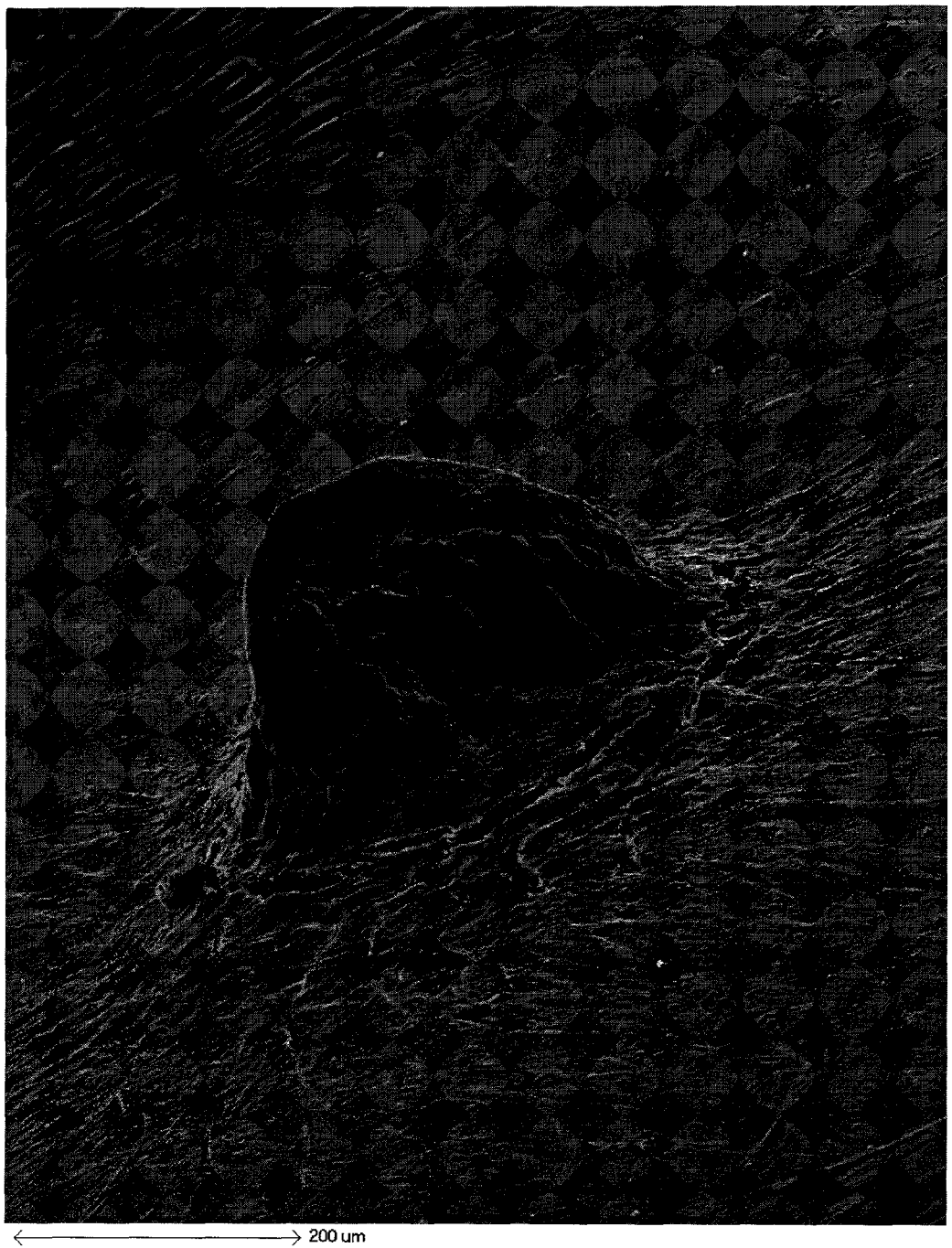
FIG. 8 is a scanning electron micrograph of a mature CFU-O on the tissue culture polystyrene surface.
Figure 9:
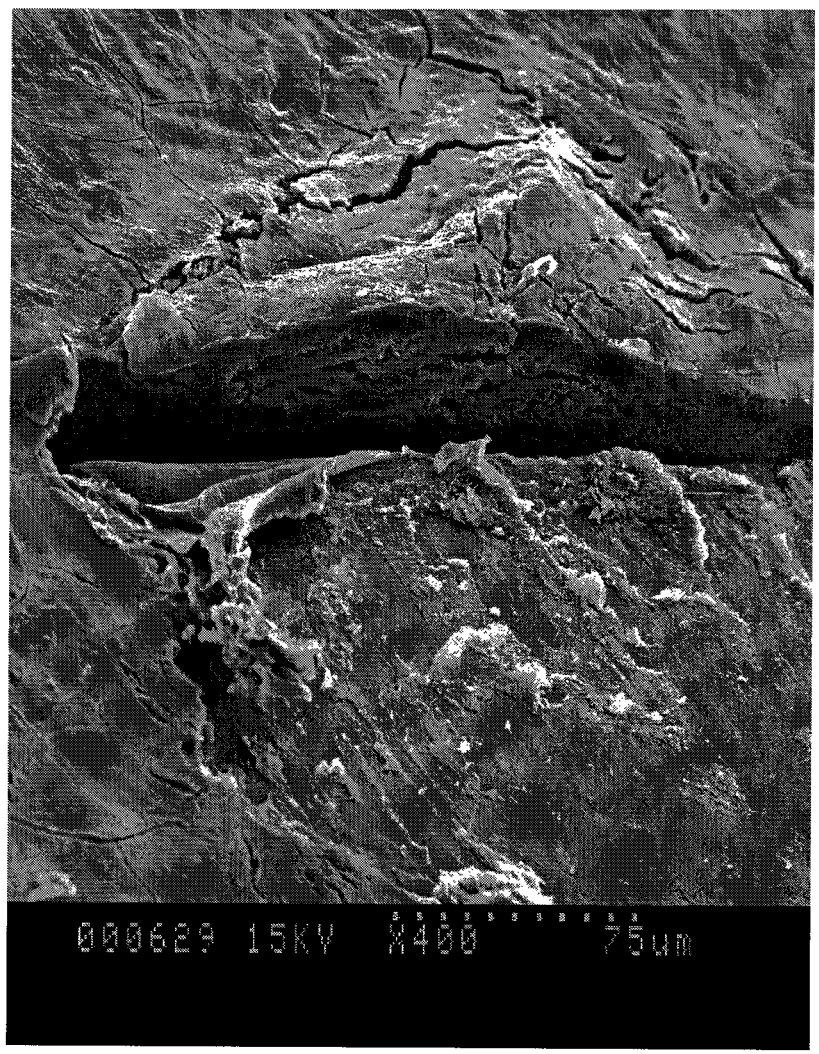
FIG. 9 is a scanning electron micrograph of a cross-section of a CFU-O exposing the underlying matrix.
Figure 10:
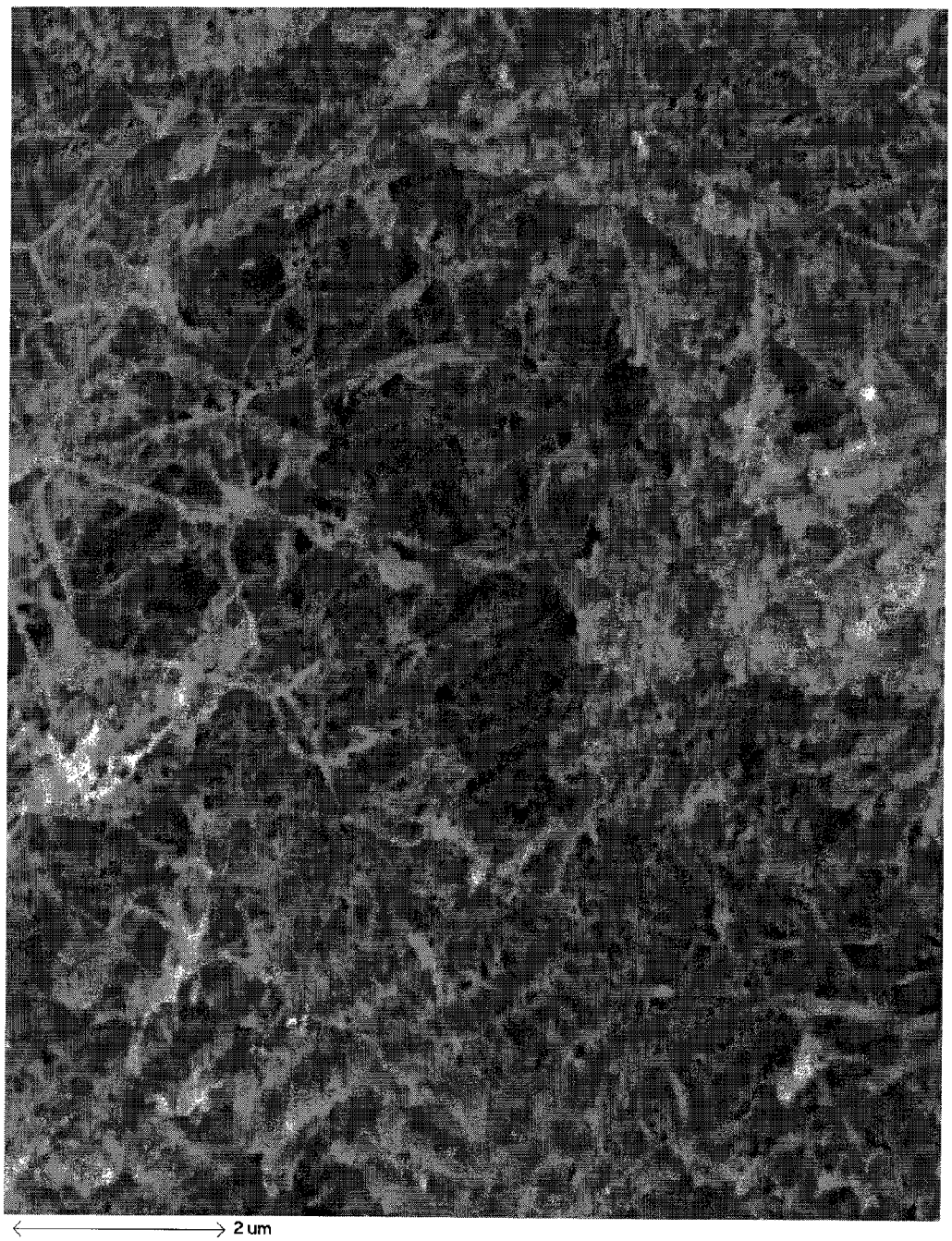
FIG. 10 is a scanning electron micrograph of the lightly mineralized collagen fibres located on the advancing edge of the CFU-O.
Figure 11:
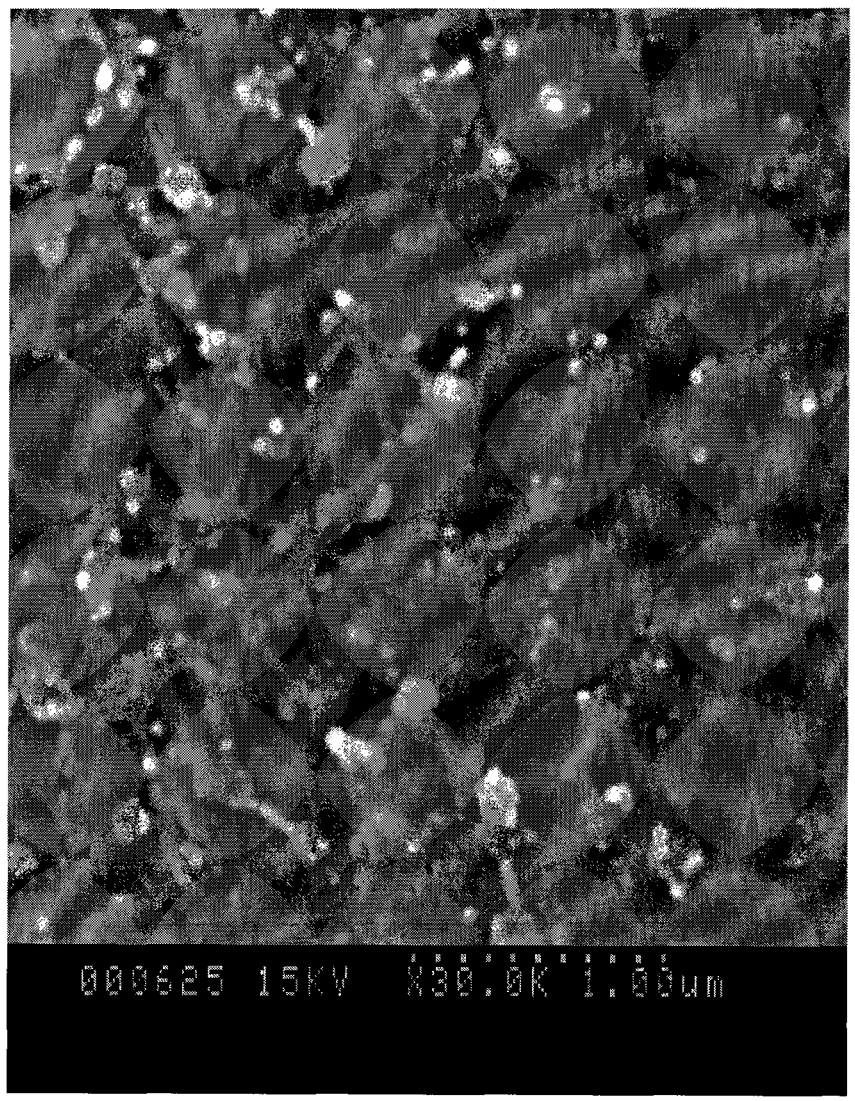
FIG. 11 is a scanning electron micrograph of the non-collagenous matrix (seen as globules) laid down on the polystyrene interface by differentiating osteogenic cells.
Figure 12:
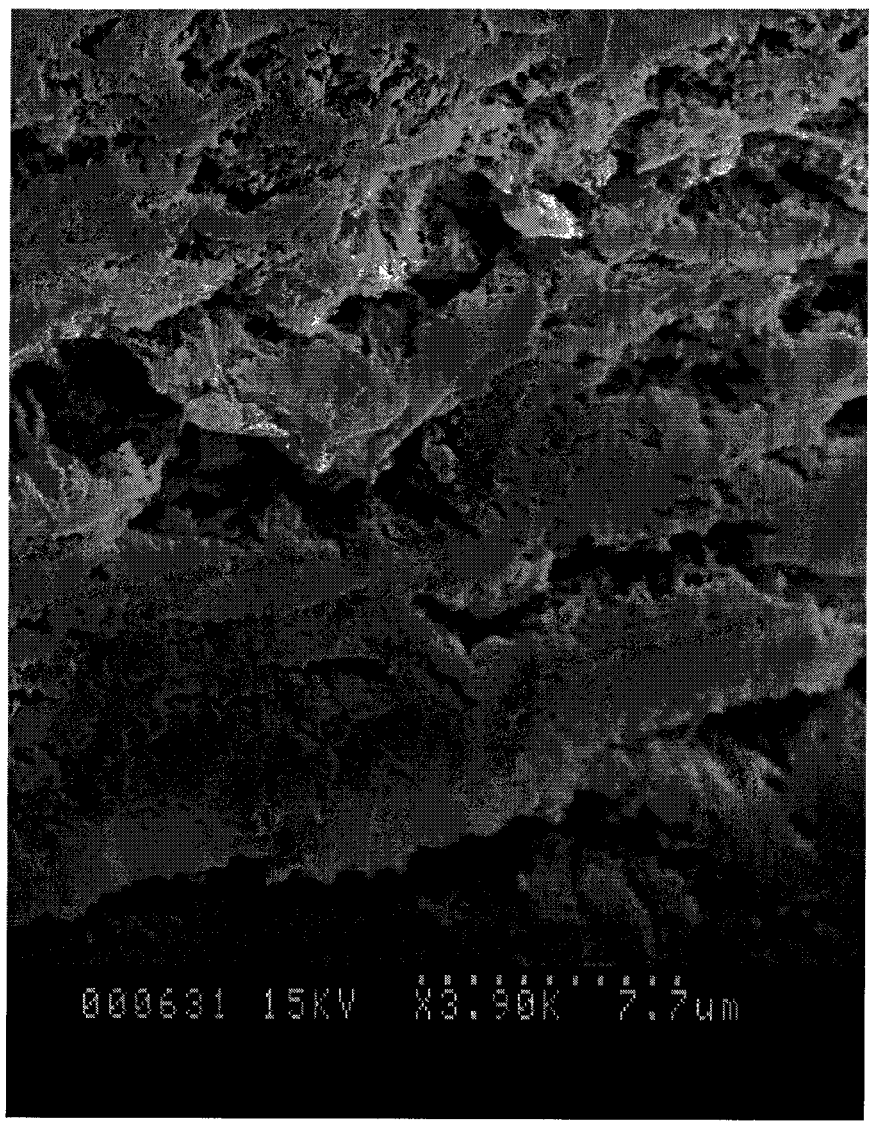
FIG. 12 is a scanning electron micrograph of heavily mineralized collagen that comprises the centre of a mature CFU-O.

Tetracycline labeling of cultures was used for labeling newly formed calcium phosphate associated with the biological mineral phase of bone. The tetracycline labeling of the cultures coincide with the mineralized nodular areas, which is visualized by exposing the cultures to UV light. FIGS. 6 and 7 depict tetracycline labeled CFU-O cultures of Day 3 and Day 5 cultures of progenitor cells. These images were generated by UV-excited fluorescence imaging, and photographed.

Scanning Electron Microscopy

The CFU-O's were observed under SEM for formation of mineralized collagen matrix which demonstrates the formation of the CFU-O's from the initial stages of collagen formation through to the densely mineralized matrix in the mature CFU-O. FIGS. 8, 9, 10, 11, 12 and 14 represent scanning electron micrographs of the CFU-Os.

Flow Cytometry & HLA-Typing

Figure 13:
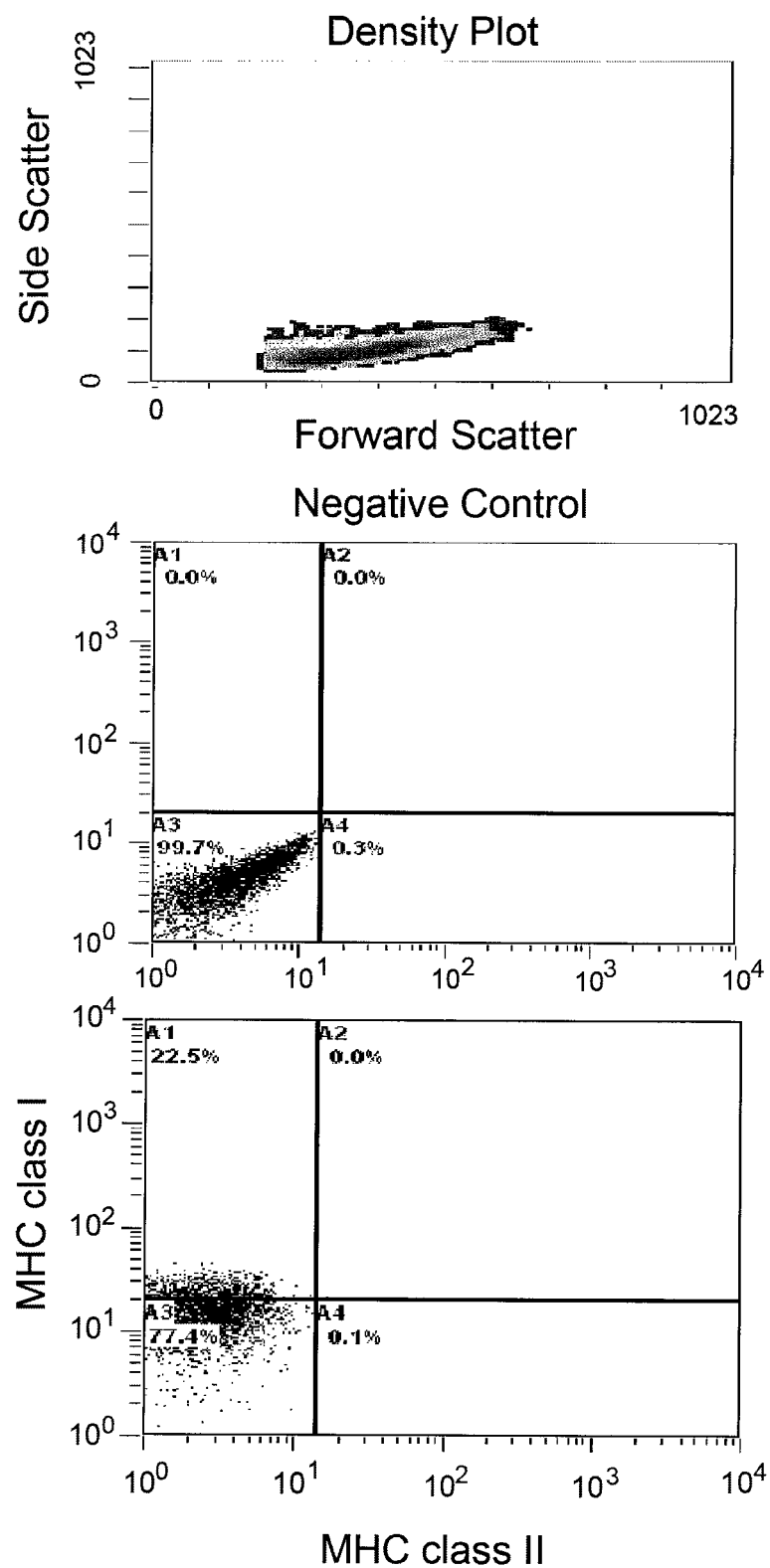
FIG. 13 illustrates the flow cytometry data demonstrating that WJ-derived cells are 77.4% MHC I and MHC II negative.
Figure 14:
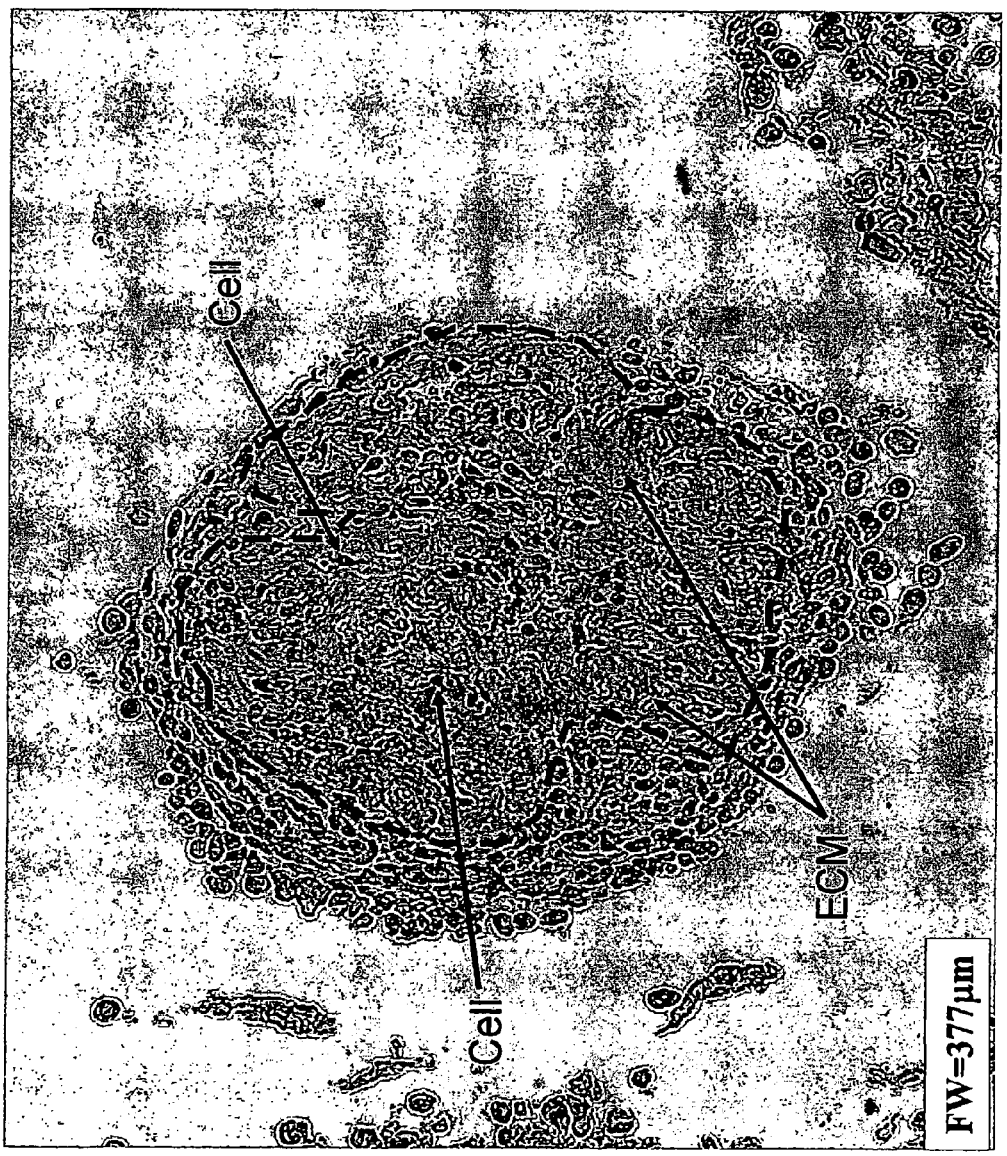
FIG. 14 is a black and white reproduction of a Masson's trichome-stained transverse section of bone nodule showing the distribution of collagen within which cells have become entrapped (osteocytes), and multilayering of peripheral cells some of which are becoming surrounded by the elaborated extracellular matrix.

The flow cytometry, identifying cell-surface antigens representing both Major Histocompatibility Complexes (MHCs) demonstrated 77.4% of the population of isolated cells as MHC$^{-/-}$. FIG. 13 illustrates the flow cytometry results in relation to the negative control. FIG. 17 shows the impact of freeze-thawing on the frequency of MHC −/− cells in the progenitor population. The effect of freeze-thawing was studied as follows:

Test cell populations of >1×10$^5$ cells were washed in PBS containing 2% FBS and re-suspended in PBS+2% FBS with saturating concentrations (1:100 dilution) of the following conjugated mouse IgG1 HLA-A,B,C-PE (BD Biosciences #555553, Lot M076246) (MHC I), HLA-DR,DP,DQ-FITC (BD Biosciences #555558, Lot M074842) (MHC II) and CD45-Cy-Cychrome (BD Biosciences #555484, Lot 0000035746) for 30 minutes at 4° C. The cell suspension was washed twice with PBS+2% FBS and re-suspended in PBS+2% FBS for analysis on a flow cytometer (XL, Beckman-Coulter, Miami, Fla.) using the ExpoADCXL4 software (Beckman-Coulter). Positive staining was defined as the emission of a fluorescence signal that exceeded levels obtained by >99% of cells from the control population stained with matched isotype antibodies (FITC-, PE-, and Cy-cychrome-conjugated mouse IgG1,κ monoclonal isotype standards, BD Biosciences), which was confirmed by positive fluorescence of human BM samples. For each sample, at least 10,000 list mode events were collected. All plots were generated in EXPO 32 ADC Analysis software.

Sub-Culture & Cell Seeding

The attached cells were sub-cultured (passaged) using 0.1% trypsin solution after 7 days, at which point they exhibited 80-90% confluency as observed by light microscopy. Upon passage, the cells were observed by flow cytometry for expression of MHC-A,B,C, MHC-DR,DP,DQ, and CD45. They were then plated in T-75 tissue culture polystyrene flasks at 4×10$^3$ cells/cm$^2$ in SM, and treated with 10$^{-8}$M Dex, 5 mM β-GP and 50 μg/ml ascorbic acid to test the osteogenic capacity of these cells. These flasks were observed on days 2, 3, 4, 5 and 6 of culture for CFU-O or bone nodule, formation. Any residual cells from the passaging procedure also were cryopreserved for future use.

Cryopreservation of Cells

Aliquots of $1\times10^6$ PVT cells were prepared in 1 ml total volume consisting of 90% FBS, 10% dimethyl sulphoxide (DMSO) (Sigma D-2650, Lot#11K2320), and pipetted into 1 ml polypropylene cryo-vials. The vials were placed into a −70° C. freezer overnight, and transferred the following day to a −150° C. freezer for long-term storage. After one week of cryo-preservation, the PVT cells were thawed and observed by flow cytometry for expression of MHC-A,B,C, MHC-DR,DP,DQ, and CD45. A second protocol was used in which the PVT cells were thawed after one week of cryo-preservation, recultured for one week, sub-cultured then reanalyzed by flow cytometry for expression of MHC-A,B, C, MHC-DR,DP,DQ, and CD45.

The results are presented in FIG. 17. It will be noted that the frequency of MHC−/− within the fresh cell population is maintained through several passages. When fresh cells are frozen after passaging, at −150° C. for one week and then immediately analyzed for MHC phenotype, this analyzed population displays a remarkably enhanced frequency of cells of the MHC −/− phenotype. Thus, and according to an embodiment of the present invention, cells of the MHC −/− phenotype can usefully be enriched from a population of PVT cells by freezing. Still further enrichment is realized upon passaging the cultures of the previously frozen cells. In particular, and as seen in FIG. 17, first passage of cryopreserved cells increases the relative population of MHC −/− cells to greater than 50% and subsequent freezing and passaging of those cells yields an MHC −/− population of greater than 80%, 85%, 90% and 95%. The frozen PVT cells per se are potentially very useful in human therapy, given their non immunogenic nature.

Harvest of Post Adherent HUCPV Cell Fraction

The yield of progenitors recovered from the perivascular tissue can be enhanced in the following manner. In order to harvest the "post adherent" (PA) fraction of HUCPV cells, the supernatant of the initially seeded HUCPV harvest was replated onto a new T-75 flask, and incubated at 37° C., 5% $CO_2$ for 2 days. The initially seeded HUCPV flask was then fed with fresh SM. After 2 days this supernatant was again transferred to a new T-75 flask, and the attached cells fed with fresh SM. Finally, the supernatant of the third seeded flask was aspirated, and this flask fed with fresh SM. (Consequently, for each cord, 3 flasks are generated: the initially seeded flask, the first PA fraction and the second PA fraction.) Similar to identical characteristics of these cells are seen compared to the initially seeded cells, confirming that higher cell yields are obtained by isolating these PA fractions. Similar to the initially seeded HUCPV cells, these PA cells have a rapid proliferation rate, spontaneously produce bone nodules in culture, and can be induced to differentiate into the other three lineages: cartilage, fat and muscle.

Tissue Engineering Compositions Comprising the Progenitor Cells

In this example, the cells are combined with a carrier in the form of CAP/PLGA used commonly in the bone engineering field. In order to seed the CAP/PLGA scaffolds, they were cut into 5 mm by 5 mm cylinders. Then, a 200 µl suspension of $2\times10^5$ HUCPV cells was placed into a sterile 1.5 ml eppendorf tube, and the scaffold placed into the suspension. Using a modified pipette tip (with a suction diameter of 5 mm), the suspension of cells was suctioned and washed through the scaffold several times by pipetting up and down. The scaffolds were then incubated in this suspension for 4 hours at 37° C., 5% $CO_2$, to allow for attachment of the cells to the scaffold. After the 4 hours, the scaffolds were removed from the suspensions and placed into individual wells of a non-tissue culture treated 24-well plate, fed with 1 ml of SM and incubated at 37° C., 5% $CO_2$ for 14 days, the SM being replaced every 2 days. The scaffolds were then fixed in Karnovsky's fixative and prepared for SEM analysis (see above). After 14 days of culture, the HUCPV cells completely covered the scaffold.

As noted, the PVT progenitor cell population may also be exploited to give rise to mesenchymal cells and tissues other than bone, by culturing under conditions appropriate for such differentiation. To generate adipocytes, for instance, the progenitors are prepared at a concentration of $10^4$ cells/cm$^2$ and plated in 35 mm tissue culture dishes. The cells are maintained in Preadipocyte Medium (PM) (DMEM/Ham's F-10 (1:1, vol/vol), 10% fetal calf serum, 15 mM HEPES, 100 U/ml penicillin, 100 µg/ml streptomycin, 0.25 µg/ml amphotericin B) for 3 days. After 3 days, the PM is removed, and the cells are fed with Adipogenic medium (DMEM/Ham's F-10 nutrient broth, 1:1, v/v; HEPES buffer (15 mM); Fetal Bovine Serum (3%); Biotin (33 µM), Pantothenate (17 µM), human insulin (100 nM), dexamethasone (0.5 µM), PPARγ agonist (1 µM) and antibiotics), and cultured for 3 days. After the 3 day induction, the Adipogenic medium is removed, and the cultures are maintained in Adipocyte Medium (AM) (DMEM/Ham's F-10 (1:1, vol/vol), 3% fetal calf serum, 1 µM dexamethasone, 100 nM human insulin, 33 µM D-biotin, 17 µM Na-pantothenate, 15 mM HEPES, 100 U/ml penicillin, 100 µg/ml streptomycin, 0.25 µg/ml amphotericin B), with regular feeding every 3 days, ensuring to only remove half the medium, replenishing with an equal volume of AM since adipocytes will float if all the media is removed. After four feedings (12 days), cells appear rounded with lipid droplets. Positive identification of differentiated mesenchymal cells into adipocytes can be confirmed by staining with Oil Red O and Nile Red.

Similarly, chondrocytes may be generated using cell suspensions prepared at a concentration of $10^4$ cells/cm$^2$ and plated in 35 mm tissue culture dishes. To promote chondrogenic cells are cultured without serum and with transforming growth factor-β3. The cell pellets develop a multilayered matrix-rich morphology and histologically show an increased proteoglycan-rich extracellular matrix during culture.

To generate myoblasts, cell suspensions are prepared at a concentration of $10^4$ cells/cm$^2$ and plated in 35 mm tissue culture dishes. The cells are maintained in MCDB 120 medium completed with 15% fetal bovine serum (FBS) for 1 week (myoblast proliferation medium, MPM). At 1 week, the serum level in the basal medium (MPM) is dropped to 2% (myoblast differentiation medium, MDM) and the cultures are terminated after 7 days. The cultures are re-fed 3-times a week with appropriate culture medium.

It will thus be appreciated that the present invention provides human progenitor cells having properties useful in the production of various connective tissues including bone, and further provides progenitor cells that are immune incompetent and ideal for transplantation into human patients to treat connective tissue conditions including bone diseases and disorders. The human progenitor cells are generated from extracts of a particular zone of human umbilical cord Wharton's jelly, termed the perivascular zone, extending proximally from the external wall of the cord vessels. The cell population extracted from this zone displays remarkable properties, including rapid proliferation, changes in cell morphology, as witnessed by the formation of cell colonies occurring before day 7 in all subcultured flasks (approximately 7-10 doublings) and the appearance of bone nodule formation without the addition of osteogenic supplements to the culture medium, as well as relatively high frequency of MHC double negative cells, the frequency of which is increased upon culturing of cells that have been frozen.

The following references are incorporated herein by reference:

REFERENCES CITED

Aubin, J E, 1998, Bone stem cells: J Cell Biochem Suppl, v. 30-31, p. 73-82.

Canfield, A E, M J Doherty, B A Ashton, 2000, Osteogenic potential of vascular pericytes, in J E Davies (ed), Bone Engineering: Toronto, E M Squared, Inc., p. 143-151.

Caplan, A I, 1991, Mesenchymal stem cells: J Orthop. Res, v. 9, p. 641-650.

Chacko, A W, S R M Reynolds, 1954, Architecture of deistended and nondistended human umbilical cord tissues, with special reference to the arteries and veins.: Carnegie Institution of Washington, Contributions to Embryology, v. 35, p. 135-150.

Conget, P, J J Minguell, 1999, Phenotypical and functional properties of human bone marrow mesenchymal progenitor cells: J. Cell Physiol, v. 181, p. 67-73.

Haynesworth, S E, D Reuben, A I Caplan, 1998, Cell-based tissue engineering therapies: the influence of whole body physiology.: Adv Drug Deliv Rev, v. 33, p. 3-14.

Kogler, G, S Sensken, J A Airey, T Trapp, M Muschen, N Feldhahn, S Liedtke, R V Sorg, J Fischer, C Rosenbaum, S Greschat, A Knipper, J Bender, 0 Degistirici, J Gao, A I Caplan, E J Colletti, G Almeida-Porada, H W Muller, E Zanjani, P Wernet, 2004, A new human somatic stem cell from placental cord blood with intrinsic pluripotent differentiation potential: J Exp. Med., v. 200, p. 123-135.

Mitchell, K E, M L Weiss, B M Mitchell, P Martin, D Davis, L Morales, B Helwig, M Beerenstrauch, K Abou-Easa, T Hildreth, D Troyer, 2003, Matrix cells from Wharton's jelly form neurons and glia: Stem Cells, v. 21, p. 50-60.

Parry, E W, 1970, Some electron microscope observations on the mesenchymal structures of full-term umbilical cord: Journal of Anatomy, v. 107, p. 505-518.

Pereda, J, P M Motta, 2002, New advances in human embryology: morphofunctional relationship between the embryo and the yolk sac: Medical Electron Microscopy, v. 32, p. 67-78.

Romanov, Y A, V A Svintsitskaya, V N Smirnov, 2003, Searching for alternative sources of postnatal human mesenchymal stem cells: Candidate MSC-like cells from umbilical cord: Stem Cells, v. 21, p. 105-110.

Schoenberg, M D, A Hinman, R D Moore, 1960, Studies on connective tissue V, Feber formation in Wharton's Jelly.: Laboratory Investigation, v. 9, p. 350-355.

Sen, A, Y R Lea-Currie, D Sujkowska, D M Franklin, W O Wilkison, Y D Halvorsen, J M Gimble, 2001, Adipogenic potential of human adipose derived stromal cells from multiple donors is heterogeneous: J. Cell Biochem., v. 81, p. 312-319.

Takechi, K, Y Kuwabara, M Mizuno, 1993, Ultrastructural and immunohistochemical studies of Wharton's jelly umbilical cord cells: Placenta, v. 14, p. 235-245.

Tuchmann-Duplessis, H, (3 David, P Haegel, 1972, Illustrated Human Embryology, New York, Springer-Verlag, p. 54-61.

Weiss, L, 1983, Histology: cell and tissue biology, New York, Elseiver Biomedical, p. 997-998.

Wharton, T W, 1656, Adenographia, Translated by Freer S. (1996). Oxford, U.K., Oxford University Press, p. 242-248.

We claim:

1. A Wharton's jelly extract, wherein the extract comprises:
   (i) a cell population, wherein the cell population comprises human progenitor cells having MHC double negative phenotype;
   (ii) a structural matrix from human umbilical cord perivascular tissue; and
   (iii) an exogenous enzyme in an amount sufficient to release the cell population from collagen matrix of the Wharton's jelly, wherein the exogenous enzyme is in contact with the structural matrix, and
   wherein the extract is essentially free from cells of umbilical cord blood.

2. The Wharton's jelly extract of claim 1, wherein the extract is obtained by subjecting umbilical cord vasculature bearing proximal Wharton's jelly to enzymatic digestion in a suitable cell extraction medium.

3. The Wharton's jelly extract of claim 2, wherein the enzymatic digestion results in the release of cells from the collagen matrix of the Wharton's jelly.

4. A Wharton's jelly extract according to claim 3, in which the extraction is performed at 37° C. in phosphate buffered saline and 0.5-10.0 mg/mL collagenase for a period of 1 to 24 hours.

5. The Wharton's jelly extract of claim 1, wherein the extract comprises human umbilical cord perivascular cells having a CD45-phenotype.

6. The Wharton's jelly extract of claim 1, wherein the extract is obtained by mechanical separation.

7. The Wharton's jelly extract of claim 1, wherein the extract obtained is minimally manipulated.

8. The Wharton's jelly extract of claim 1, wherein the exogenous enzyme is collagenase.

9. The Wharton's jelly extract of claim 1, wherein the extract is present in a cryopreserved state.

10. The Wharton's jelly extract of claim 1, wherein the extract is essentially free from cells derived from the vascular structure of the human umbilical cord.

11. The Wharton's jelly extract of claim 1, wherein the extract is enriched for progenitor cells having an MHC double negative phenotype.

12. The Wharton's jelly extract of claim 11, wherein at least 50% of the cells in the extract have an MHC double negative phenotype.

13. The Wharton's jelly extract of claim 12, wherein at least 80% of the cells in the extract have an MHC double negative phenotype.

14. The Wharton's jelly extract of claim 13, wherein at least 90% of the cells in the extract have an MHC double negative phenotype.

15. The Wharton's jelly extract of claim 1, wherein the extract exhibits a disrupted extracellular matrix architecture.

16. The Wharton's jelly extract of claim 1, wherein the extract comprises a carrier.

17. The Wharton's jelly extract of claim 1, wherein the cell population comprises cells further characterized by expression of one or more of the following markers: CD34−, SH2+, SH3+, Thy1+, alpha-actin+, desmin+, and vimentin+.

18. The Wharton's jelly extract of claim 1, wherein the progenitor cells are osteoprogenitor cells, chondrogenic progenitor cells, adipogenic progenitor cells, or myogenic progenitor cells.

19. The Wharton's jelly extract of claim 1, wherein the progenitor cells are capable of differentiating into bone-, fat-, cartilage-, tendon-, or muscle-producing cells.

20. The Wharton's jelly extract of claim 1, wherein the cell population is obtainable from perivascular region of at least one human umbilical cord blood vessel.

\* \* \* \* \*